(12) United States Patent
Schendzielorz et al.

(10) Patent No.: US 9,644,226 B2
(45) Date of Patent: May 9, 2017

(54) METHOD FOR PRODUCING VECTORS CONTAINING A GENE CODING FOR AN ENZYME HAVING REDUCED OR DEACTIVATED FEEDBACK INHIBITION AND THE USE THEREOF FOR PRODUCING AMINO ACIDS AND NUCLEOTIDES

(71) Applicant: Forschungszentrum Juelich GmbH, Juelich (DE)

(72) Inventors: Georg Schendzielorz, Duesseldorf (DE); Stephan Binder, Eschweiler (DE); Lothar Eggeling, Juelich (DE); Michael Bott, Juelich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 14/422,394

(22) PCT Filed: Jul. 23, 2013

(86) PCT No.: PCT/DE2013/000416
§ 371 (c)(1),
(2) Date: Feb. 19, 2015

(87) PCT Pub. No.: WO2014/029376
PCT Pub. Date: Feb. 27, 2014

(65) Prior Publication Data
US 2015/0284760 A1    Oct. 8, 2015

(30) Foreign Application Priority Data

Aug. 22, 2012 (DE) .................. 10 2012 016 716

(51) Int. Cl.
| | | |
|---|---|---|
| C12N 15/63 | (2006.01) | |
| C12N 15/00 | (2006.01) | |
| C12N 15/64 | (2006.01) | |
| C12P 19/34 | (2006.01) | |
| C12N 9/02 | (2006.01) | |
| C12N 9/12 | (2006.01) | |
| C12P 13/08 | (2006.01) | |

(52) U.S. Cl.
CPC ............ C12P 19/34 (2013.01); C12N 9/1217 (2013.01); C12P 13/08 (2013.01); C12Y 207/02004 (2013.01); Y02P 20/52 (2015.11)

(58) Field of Classification Search
None
See application file for complete search history.

(56) References Cited

U.S. PATENT DOCUMENTS

| | | | |
|---|---|---|---|
| 3,919,189 A | 11/1975 | Empey et al. | |
| 4,822,738 A | 4/1989 | Miwa et al. | |
| 5,213,972 A | 5/1993 | McCandliss et al. | |
| 5,804,414 A | 9/1998 | Moriya et al. | |
| 7,169,586 B2 | 1/2007 | Ptitsyn et al. | |
| 2014/0259212 A1* | 9/2014 | Plesch ................ | C12N 15/8243 800/278 |

FOREIGN PATENT DOCUMENTS

| | | |
|---|---|---|
| CA | 2 663 711 | 4/2008 |
| DE | 10 2008 040 352 | 1/2010 |
| EP | 0 088 424 | 9/1983 |
| EP | 0 381 527 | 2/1990 |
| EP | 1 026 247 | 8/2000 |
| EP | 1 067 191 | 1/2001 |
| EP | 1 097 998 | 5/2001 |
| EP | 1 529 839 | 5/2005 |
| EP | 1 568 776 | 8/2005 |
| EP | 1 942 183 | 7/2008 |
| EP | 2 147 972 | 1/2010 |
| EP | 1 745 138 | 5/2010 |
| JP | 6-62866 | 3/1994 |
| RU | 2003677 | 11/1993 |
| RU | 2119536 | 9/1998 |
| WO | WO-01/49854 | 7/2001 |
| WO | WO-03/027310 | 4/2003 |
| WO | WO-2011/138006 | 11/2011 |

OTHER PUBLICATIONS

Binder et al, A high-throughput approach to identify genomic variants of bacterial metabolite producers at the single-cell level, Genome Biology, 2012, pp. 1-12.*
Huijser et al, The Arabidopsis Sucrose Uncoupled-6 gene is identical to Anscisic Acid Insensitive-4: involvement of abscisic acid in sugar responses, The Plant Journal, 200, vol. 23(5), 577-585.*
Van Oosten et al, An Arabidopsis mutant showing reduced feedback inhibition of photosynthesis, The Plant Journal, 1997, pp. 1011-1020.*
Takagi et al, PCR random mutagenesis into Escherichia coli serine acetyltransferase : isolation of the mutant enzymes that cause overproduction of L-cysteine and L-cystine due to the desensitizationto feedback inhibition, FEBS Letters, 1999, pp. 323-327.*
A Method for Random Mutagenesis of a Defined DNA Segment Using a Modified Polymerase Chain Reaction Techniques 1: A Journal of Methods in Cell and Molecular Biology; (Aug. 1989) pp. 11-15—vol. 1, No. 1 David W. Leung, Ellson Chen, David V. Goeddel.
Part VII—Experiments Handbook of Corynebacterium glutamicum (eds. Eggeling and Bott), in Section 23 on pp. 535-566.

(Continued)

Primary Examiner — Maria Marvich
(74) Attorney, Agent, or Firm — Jordan and Koda, PLLC

(57) ABSTRACT

A method for producing vectors containing a gene coding for an enzyme having reduced or deactivated feedback inhibition and to the use thereof for producing amino acids and nucleotide. Genes coding for feedback-inhibited enzymes are mutagenized in vitro, —ligated into vectors in a further step—the vectors are each transformed in a microorganism containing a metabolite sensor in a further step, which brings about the synthesis of a fluorescent protein at an increased metabolite concentration, —whereupon microorganisms exhibiting increased or maximum fluorescence are selected; and —the vectors that contain a gene coding for an enzyme having reduced or deactivated feedback inhibition are isolated from microorganisms having increased or maximum fluorescence.

13 Claims, No Drawings

(56) References Cited

OTHER PUBLICATIONS

Corynebacterium glutamicum DNA is subjected to methylation-restriction in *Escherichia coli* Andreas Tach, et al. (FEMS Microbiology Letters 123, pp. 343-347 (1994).
Overproduction of L-Cysteine and L-Cystine by *Escherichia coli* strains with a Genetically Altered Serine Acetyltransferase Shigeru Nakamori et al.; 1998, Appl Env. Microbiol. 64: 1607-1611.
Tightly regulated tac promoter vectors useful for the expression of unfused and fused proteins in *Escherichia coli* Egon Amann et al.: Gene 69L 301-315 (1988).
The Complete Genome Sequence of *Escherichia coli* K-12 Frederick Blattner et al., (Science 277: 1453-1452 (1997).
Gapped BLAST and PSI-BLAST: a new generation of protein database search programs Stephen F. Altschul, et al.: 1997, Nucleic Acids Res. 25(17): 3389-3402.
Cloning of the ATP Phosphoribosyl Transferase Gene of Corynebacterium glutamicum and Application of the Gene to L-Histidine Production Toru Mizukami, et al.: Biosci Biotechnol Biochem, Apr. 1994 58(4): 635-8.
Transfer of Brevibacterium divaricatum DSM 20297T, "Brevibacterium flavum" DSM 20411, "Brevibacterium lactofermentum" DSM 20412 and DSM 1412, and Corynebacterium lilium DSM 20137T to Corynebacterium glutamicum and Their Distinction by rRNA Gene Restriction Patterson W. Liebl, et al. (International Journal of Systematic Bacteriology 41: 255-260 (1991).
Construction and properties of a family of pACYC184-derived cloning vectors compatible with pBR322 and its derivatives Borja Bartolome et al.: Gene 102, pp. 75-78 (1991).
Primary structure of the essential replicon of the plasmid pSC101 Cathy Vocke and Deepak Bastia.: Proceedings of the National Academy of Sciences USA 80(21): pp. 6557-6561: 1983.
Randomization of Genes by PCR Mutagenesis R,. Craig et al.: 1992 PCT Methods Applications 2: pp. 28-33.
Stable Expression of hom-1-thrB in Corynebacterium glutamicum and Its Effect on the Carbon Flux to Threonine and Related Amino Acids Dieter J. Reinscheid, et.: (Applied and Environmental Microbiology 60, 126-132 (1994).
Plasmids in Lactobacillus Tsung-Tsan Wang et al. and Byong H. Lee, 1997, Crit Rev Biotechnol, 17(3), pp. 227-272.
Kanamycin-resistant vectors that are analogues of plasmids pUC8, pUC9, pEMBL8 and pEMBL9 (Recombinant DNA; multi-linkers; f1 intergenic region; lacZx-complementation) Brian G. Spratt et al. 1986, Gene 41: 337-342.
The F Plasmid CcdB Protein Induces Efficient ATP-dependent DNA Cleavage by Gyrase Phillippe Bernard, et al.: Firma Invitrogen, Groningen, Netherlands: Hournal of Molecular Biology, 234: pp. 534-541 (1993).
Transformation of spheroplasts and protoplasts of Corynebacterium glutamicum Georg Thierbach et al. (Applied Microbiology and Biotechnology 29, pp. 356-362 (1988).
PCR random mutagenesis into *Escherichia coli* serine acetyltransferase: isolation of the mutant enzymes that cause overproduction of L-cysteine and L-cystine due to the desensitization to feedback inhibition Hiroshi Takagi et al., 1999, FEBS Lett. 452: 323-327.
A Broad Host Range Mobilization System for In Vivo Genetic Engineering: Transposon Mutagenesis in Gram Negative Bacteria R. Simon, et al., Bio/Technology 1, 784-791, 1983.
Small mobilizable multi-purpose cloning vectors derived from the *Escherichia coli* plasmids pK18 and pK19: selection of defined deletions in the chromosome of Corynebacterium glutamicum Andreas Schaefer, et al., (Applied and Environmental Microbiology 60, 756-759 (1994).
A functionally Split Pathway for Lysine Synthesis in Corynebacterium glutamicum Barbel Schrumpf, et al. 1991, Journal of Bacteriology 173: 4510-4516.
Corynebacterium glutamicum DNA is subjected to methylation-restriction in *Escherichia coli* Andreas Tauch, et al.: (FEMS Microbiology Letters 123, 343-347 (1984).
High Frequency Transformation of Whole Cells of Amino Acid Producing Coryneform Bacteria Using High Voltage Electroporation L. Kieran Dunican and Emer Shivnan, (Bio/Technology 7, 1067-1070 (1989).
Basic Local Alignment Search Tool (BLAST) Stephen F. Altschul, et al. J. Mol. Biol. 1990, 215-, 403-410.
Differential plasmid rescue from transgenic mouse DNAs into *Escherichia coli* methylation-restriction mutants Seth G. N. Grant et al., 1990, Proceedings of the National Academy of Sciences U.S.A., 87: 4645-4649.
Isoleucine Synthesis in Corynebacterium glutamicum: Molecular Analysis of the ilvB-ilvN-ilvC Operon Carmen Keilhauer, et al., in J. Bacteriol, Sep. 1993: 175(17): 5595-603.
Issues in searching molecular sequence databases Stepehn F. Altchul, et al., (Nature Genetics 6, 119-129 (1994).
Fidelity of DNA Synthesis by the Thermus aquaticus DNA Polymerase Kenneth R. Tindal and Thomas A. Kunkel, Biochemistry, 1998, 27(16): p. 6008-13.
Random Matagenesis Methods for In Vitro Directed Enzyme Evolution Nikolaos E. Labrou, Curr Protein Pept Sci. 2010;11: 91-100.
Novel Approach to Molecular Cloning and Polynucleotide Synthesis Using Vaccinia DNA Topoisomerase Stewart Shuman, (1994), Journal of Biological Chemistry 269: 32678-84.
Tools for genetic engineering in the amino acid-producing bacterium Corynebacterium glutamicum Oliver Kirschner and Andreas Tausch, (J. Biotechnol. Sep. 4, 2003; 104 (1-3); 287-299.
Improved tools for biological sequence comparison William R. Pearson and David J. Lipman (Proceedings of the National Academy of Sciences USA 85) pp. 2444-2448 (1998).
Extraction and Purification of Plasmid DNA—Plasmid Vectors (1.21-1.28 pgs.) (Sambrooket al., Molecular Cloning. A Laboratory Manual (1989) Cold Spring Harbor Laboratory Press, Cold Spring Harbor, NY, USA).
Stephan Binder et al: "A high-throughput approach to identify genomic variants of bacterial metabolite producers at the single-cell level", Genome Biology, Biomed Central Ltd., London, GB. vol. 13, No. 5, May 28, 2012 (May 28, 2012), p. R40, XP021127741, ISSN: 1465-6906, DOI: 10.1186/GB-2012-13-5-R40 p. 3-p. 6; figure 2, p. 10.
Nurije Mustafi et al: "The development and application of a single-cell biosensor for the detection of—methionine and branched-chain amino acids", Metabolic Engineering, Academic Press, US, vol. 14, No. 4, Feb. 6, 2012 (Feb. 6, 2012), pp. 449-457, XP028429545, ISSN: 1096-7176, DOI: 10.1016/J.YMBEN.2012. 02.002 [retrieved on Feb. 15, 2012] p. 454-p. 456; figures 3, 4.
High-throughput enzyme evolution in *Saccharomyces cerevisiae* using a synthetic RNA switch Joshua K. Michener, et al. Metabolic Engineering 14 (2012) pp. 306-316.

\* cited by examiner

SEQUENCE LISTING

<160> NUMBER OF SEQ ID NOS: 34

<210> SEQ ID NO 1
<211> LENGTH: 35
<212> TYPE: DNA
<213> ORGANISM: artificial
<220> FEATURE:
<223> OTHER INFORMATION: Primer

<400> SEQUENCE: 1
gatggatccg tggccctggt cgtacagaaa tatgg    35

<210> SEQ ID NO 2
<211> LENGTH: 34
<212> TYPE: DNA
<213> ORGANISM: artificial
<220> FEATURE:
<223> OTHER INFORMATION: Primer

<400> SEQUENCE: 2
gatgtcgact tagcgtccgg tgcctgcata aacg    34

<210> SEQ ID NO 3
<211> LENGTH: 23
<212> TYPE: DNA
<213> ORGANISM: artificial
<220> FEATURE:
<223> OTHER INFORMATION: Primer

<400> SEQUENCE: 3
cacaggaaac agctatgacc atg    23

<210> SEQ ID NO 4

```
<211> LENGTH: 24
<212> TYPE: DNA
<213> ORGANISM: artificial
<220> FEATURE:
<223> OTHER INFORMATION: Primer

<400> SEQUENCE: 4
cgccagggtt tcccagtca cgac                                            24

<210> SEQ ID NO 5
<211> LENGTH: 73
<212> TYPE: DNA
<213> ORGANISM: artificial
<220> FEATURE:
<223> OTHER INFORMATION: Primer

<400> SEQUENCE: 5
gccctcgaga aaacaaaagg ctcagtcgga agactgggcc ttttgttttg gtaccagcgg    60
cagcgtgaac atc                                                       73

<210> SEQ ID NO 6
<211> LENGTH: 39
<212> TYPE: DNA
<213> ORGANISM: artificial
<220> FEATURE:
<223> OTHER INFORMATION: Primer

<400> SEQUENCE: 6
gccgtcgaca cggaattcaa tcttacggcc tgcggaacg                           39

<210> SEQ ID NO 7
<211> LENGTH: 21
<212> TYPE: DNA
<213> ORGANISM: artificial
<220> FEATURE:
<223> OTHER INFORMATION: Primer

<400> SEQUENCE: 7
tgagacgcat ccgctaaagc c                                              21

<210> SEQ ID NO 8
<211> LENGTH: 22
<212> TYPE: DNA
<213> ORGANISM: artificial
<220> FEATURE:
<223> OTHER INFORMATION: Primer

<400> SEQUENCE: 8
atcttacggc ctgcggaacg tg                                             22

<210> SEQ ID NO 9
<211> LENGTH: 1266
<212> TYPE: DNA
<213> ORGANISM: Corynebacterium glutamicum

<400> SEQUENCE: 9
gtggccctgg tcgtacagaa atatggcggt tcctcgcttg agagtgcgga acgcattagc    60
gacgtcgctg aacggatcgt tgccaccaag aaggctggaa atgatgtcgt ggttgtctgc   120
tccgcaatgg gagacaccac ggatgaactt ctagaacttg cagcggcagt gaatcccgtt   180
ccgccagctc gtgaaatgga tatgctcctg actgctggtg agcgtatttc tagcgctctc   240
gtcgccatgc tattgagtc ccttggcgca gaagcccaat ctttcacggg ctctcaggct   300
ggtgtgctca ccaccgagcg ccacggaaac gcacgcattg ttgatgtcac tccaggtcgt   360
```

```
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg ctttgaacgc tgatgtgtgt gagatttact cggacgttga cggtgtgtat    540
accgctgacc cgcgcgtcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtctttata gtaatgatcc cggcactttg    720
attgccggct ctatggagga tattcctgtg aagaagcag tccttaccgg tgtcgcaacc    780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc accttcacct gccctcgttc cgacggccgc    960
cgcgcgatgg agatcttgaa ggagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266
```

<210> SEQ ID NO 10
<211> LENGTH: 421
<212> TYPE: PRT
<213> ORGANISM: Corynebacterium glutamicum

<400> SEQUENCE: 10

```
Val Ala Leu Val Val Gln Lys Tyr Gly Gly Ser Ser Leu Glu Ser Ala
1               5                   10                  15

Glu Arg Ile Ser Asp Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Ser Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Val Val Pro Asn Ala Gln Lys
            180                 185                 190

Leu Glu Lys Leu Ser Phe Glu Glu Met Leu Glu Leu Ala Ala Val Gly
        195                 200                 205
```

```
Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
    275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Glu Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
    355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
                420

<210> SEQ ID NO 11
<211> LENGTH: 1266
<212> TYPE: DNA
<213> ORGANISM: Corynebacterium glutamicum

<400> SEQUENCE: 11
gtggccctgg tcgtacagaa atatggcggt tcctcgcttg agagtgcgga acgcattagc      60
gacgtcgctg aacggatcgt tgccaccaag aaggctggaa atgatgtcgt ggttgtctgc     120
tccgcaatgg agacaccac  ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat ctttcacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg gaagaagcag tccttaccgg tgtcgcaacc     780
gacaagtccg aagccaaagt aaccgttctg ggtatttccg ataagccagg cgaggctgcg     840
```

-continued

```
aaggttttcc gtgcgttggc tgatgcagaa atcaacattg acatggttct gcagaacgtc    900
tcttctgtag aagacggcac caccgacatc atcttcacct gccctcgttc cgacggccgc    960
cgcgcgatgg agatcttgaa gaagcttcag gttcagggca actggaccaa tgtgctttac   1020
gacgaccagg tcggcaaagt ctccctcgtg ggtgctggca tgaagtctca cccaggtgtt   1080
accgcagagt tcatggaagc tctgcgcgat gtcaacgtga acatcgaatt gatttccacc   1140
tctgagattc gtatttccgt gctgatccgt gaagatgatc tggatgctgc tgcacttgca   1200
ttgcatgagc agttccagct gggcggcgaa gacgaagccg tcgtttatgc aggcaccgga   1260
cgctaa                                                              1266
```

<210> SEQ ID NO 12
<211> LENGTH: 421
<212> TYPE: PRT
<213> ORGANISM: Corynebacterium glutamicum

<400> SEQUENCE: 12

```
Val Ala Leu Val Val Gln Lys Tyr Gly Gly Ser Ser Leu Glu Ser Ala
1               5                   10                  15

Glu Arg Ile Ser Asp Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
```

```
            290                 295                 300
Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Leu Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 13
<211> LENGTH: 1266
<212> TYPE: DNA
<213> ORGANISM: Corynebacterium glutamicum

<400> SEQUENCE: 13
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg agacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttt cacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg aagaagcag tccttaccgg tgtcgcaacc     780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca ctggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266
```

<210> SEQ ID NO 14
<211> LENGTH: 421
<212> TYPE: PRT
<213> ORGANISM: Corynebacterium glutamicum

<400> SEQUENCE: 14

```
Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380
```

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 15
<211> LENGTH: 1266
<212> TYPE: DNA
<213> ORGANISM: Corynebacterium glutamicum

<400> SEQUENCE: 15

```
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat ctttcacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgtttggg cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg aagaagcag tccttaccgg tgtcgcaacc     780
gacaagtccg aagccaaagt aaccgttctg ggtatttccg ataagccagg cggggctgtg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266
```

<210> SEQ ID NO 16
<211> LENGTH: 421
<212> TYPE: PRT
<213> ORGANISM: Corynebacterium glutamicum

<400> SEQUENCE: 16

Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30

Gly Asn Asp Val Val Val Cys Ser Ala Met Gly Asp Thr Thr Asp
            35                  40                  45

Glu Leu Leu Glu Leu Ala Ala Ala Val Asn Pro Val Pro Pro Ala Arg

```
                50                  55                  60
Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
                100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
        130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Gly Ala Val Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 17
<211> LENGTH: 1266
<212> TYPE: DNA
<213> ORGANISM: Corynebacterium glutamicum

<400> SEQUENCE: 17
```

```
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg agacaccac ggatgaactt ctagaacttg cagcggcagt gaatcccgtt      180
ccgccagctc gtgaaatgga tatgctcctg actgctggtg agcgtatttc taacgctctc     240
gtcgccatgg ctattgagtc ccttggcgca gaagcccaat ctttcacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg aagaagcag tccttaccgg tgtcgcaacc      780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc atcttcacct gccctcgttc cgacggccgc     960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266
```

<210> SEQ ID NO 18
<211> LENGTH: 421
<212> TYPE: PRT
<213> ORGANISM: Corynebacterium glutamicum

<400> SEQUENCE: 18

```
Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140
```

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
            165                 170                 175

Asp Gly Val Tyr Thr Ala Asp Pro Arg Ile Val Pro Asn Ala Gln Lys
        180                 185                 190

Leu Glu Lys Leu Ser Phe Glu Glu Met Leu Glu Leu Ala Ala Val Gly
    195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
                420

<210> SEQ ID NO 19
<211> LENGTH: 1266
<212> TYPE: DNA
<213> ORGANISM: Corynebacterium glutamicum

<400> SEQUENCE: 19
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttttcacgg gctctcaggct     300 ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgtttggg cgtggtggtt ctgacaccac tgcagttgcg     480
ttggcagctg ctttgaacgc tgatgtgtgt gagatttact cggacgttga cggtgtgtat     540

```
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcactttg    720
attgccggct ctatggagga tattcctgtg aagaagcag tccttaccgg tgtcgcaacc     780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc atcttcacct gccctcgttc cgacggccgc    960
cgcgcgatgg agatcttgaa gaagcttcag gttcagggca actggaccaa tgtgctttac   1020
gacgaccagg tcggcaaagt ctccctcgtg ggtgctggca tgaagtctca cccaggtgtt   1080
accgcagagt tcatggaagc tctgcgcgat gtcaacgtga acatcgaatt gatttccacc   1140
tctgagattc gtatttccgt gctgatccgt gaagatgatc tggatgctgc tgcacttgca   1200
ttgcatgagc agttccagct gggcggcgaa gacgaagccg tcgtttatgc aggcaccgga   1260
cgctaa                                                              1266
```

<210> SEQ ID NO 20
<211> LENGTH: 421
<212> TYPE: PRT
<213> ORGANISM: Corynebacterium glutamicum

<400> SEQUENCE: 20

```
Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240
```

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Leu Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 21
<211> LENGTH: 1266
<212> TYPE: DNA
<213> ORGANISM: Corynebacterium glutamicum

<400> SEQUENCE: 21
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg agacaccac ggatgaactt ctagaacttg cagcggcagt gaatcccgtt     180
ccgccagctc gtgaaatgga tatgctcctg actgctggtg agcgtatttc taacgctctc     240
gtcgccatgc tattgagtc ccttggcgca gaagcccaat cttcacggg ctctcaggct      300 ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtcttata gtaatgatcc cggcactttg     720
attgccggct ctatggagga tattcctgtg aagaagcag tccttaccgg tgtcgcaacc     780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca ctggaccaa tgtgctttac    1020

```
gacgaccagg tcggcaaagt ctccctcgtg ggtgctggca tgaagtctca cccaggtgtt    1080
accgcagagt tcaaggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                                1266
```

<210> SEQ ID NO 22
<211> LENGTH: 421
<212> TYPE: PRT
<213> ORGANISM: Corynebacterium glutamicum

<400> SEQUENCE: 22

```
Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
```

```
                    325             330             335
Asn Val Leu Tyr Asp Asp Gln Val Gly Lys Val Ser Leu Val Gly Ala
            340             345             350

Gly Met Lys Ser His Pro Gly Val Thr Ala Glu Phe Lys Glu Ala Leu
            355             360             365

Arg Asp Val Asn Val Asn Ile Glu Leu Ile Ser Thr Ser Glu Ile Arg
        370             375             380

Ile Ser Val Leu Ile Arg Glu Asp Asp Leu Asp Ala Ala Ala Arg Ala
385             390             395             400

Leu His Glu Gln Phe Gln Leu Gly Gly Glu Asp Glu Ala Val Val Tyr
            405             410             415

Ala Gly Thr Gly Arg
            420

<210> SEQ ID NO 23
<211> LENGTH: 1266
<212> TYPE: DNA
<213> ORGANISM: Corynebacterium glutamicum

<400> SEQUENCE: 23
gtggccctgg tcgtacagaa atatggcggt tcctcgcttg agagtgcgga acgcattaga       60
aacgtcgctg acggatcgt tgccaccaag aaggctggaa atgatgtcgt ggttgtctgc      120
tccgcaatgg agacaccac ggatgaactt ctagaacttg cagcggcagt gaatcccgtt      180
ccgccagctc gtgaaatgga tatgctcctg actgctggtg agcgtatttc taacgctctc      240
gtcgccatgc tattgagtc ccttggcgca gaagcccaat cttccacggg ctctcaggct      300
ggtgtgctca ccaccgagcg ccacggaaac gcacgcattg ttgatgtcac tccaggtcgt      360
gtgcgtgaag cactcgatga gggcaagatc tgcattgttg ctggtttcca gggtgttaat      420
aaagaaaccc gcgatgtcac cacgttgggt cgtggtggtt ctgacaccac tgcagttgcg      480
ttggcagctg cttttgaacgc tgatgtgtgt gagatttact cggacgttga cggtgtgtat      540
accgctgacc cgcgcatcgt tcctaatgca cagaagctgg aaaagctcag cttcgaagaa      600
atgctggaac ttgctgctgt tggctccaag attttggtgc tgcgcagtgt tgaatacgct      660
cgtgcattca atgtgccact tcgcgtacgc tcgtcttata gtaatgatcc cggcactttg      720
attgccggct ctatggagga tattcctgtg aagaagcag tccttaccgg tgtcgcaacc      780
gacaagtccg aagccaaagt aaccgttctg ggtatttccg ataagccagg cgaggctgcg      840
aaggttttcc gtcgcgttgg ctgatgcagaa atcaacattg acatggttct gcagaacgtc      900
tcttctgtag aagacggcac caccgacatc atcttcacct gccctcgttc cgacggccgc      960
cgcgcgatgg agatcttgaa gaagcttcag gttcagggca actggaccaa tgtgctttac     1020
gacgaccagg tcggcaaagt ctccctcgtg ggtgctggca tgaagtctca cccaggtgtt     1080
accgcagagt tcatggaagc tctgcgcgat gtcaacgtga acatcgaatt gatttccacc     1140
tctgagattc gtatttccgt gctgatccgt gaagatgatc tggatgctgc tgcacgtgca     1200
ttgcatgagc agttccagct gggcggcgaa gacgaagccg tcgtttatgc aggcaccgga     1260
cgctaa                                                                1266

<210> SEQ ID NO 24
<211> LENGTH: 421
<212> TYPE: PRT
<213> ORGANISM: Corynebacterium glutamicum

<400> SEQUENCE: 24
```

-continued

```
Val Ala Leu Val Val Gln Lys Tyr Gly Gly Ser Ser Leu Glu Ser Ala
1               5                   10                  15

Glu Arg Ile Arg Asn Val Ala Gly Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
50                      55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415
```

Ala Gly Thr Gly Arg
        420

<210> SEQ ID NO 25
<211> LENGTH: 1266
<212> TYPE: DNA
<213> ORGANISM: Corynebacterium glutamicum

<400> SEQUENCE: 25

```
gtggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgttcctg actgctggtg agcgtatttc taacgctctc     240
gtcgccatgg ctattgagtc ccttggcgca gaagcccaat cttttcacgg gctctcaggct    300
ggtgtgctca ccaccgagcg ccacggaaac gcacgcattg ttgatgtcac tccaggtcgt     360
gtgcgtgaac cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg cttttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag gttttggtgc tgcgcagtgt tgaatacgct     660
cgtgcattca atgtgccacc tcgcgtacgc tcgtcttata gtgatgatcc cggcactttg     720
attgccggct ctatggagga tattcctgtg gaagaagcag tccttaccgg tgtcgcaacc     780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca actggaccaa tgtgctttac    1020
gacgaccagg tcggcaaagt ctccctcgcg ggtgctggac tgaagtctca cccaggtgtt    1080
accgcagagt tcatggaagc tctgcgcgat gtcaacgtgg acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266
```

<210> SEQ ID NO 26
<211> LENGTH: 421
<212> TYPE: PRT
<213> ORGANISM: Corynebacterium glutamicum

<400> SEQUENCE: 26

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Phe Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr

```
            85                  90                  95
Gly Ser Gln Ala Gly Val Leu Thr Thr Glu Arg His Gly Asn Ala Arg
            100                 105                 110

Ile Val Asp Val Thr Pro Gly Arg Val Arg Glu Pro Leu Asp Glu Gly
            115                 120                 125

Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                    165                 170                 175

Asp Gly Val Tyr Thr Ala Asp Pro Arg Ile Val Pro Asn Ala Gln Lys
                    180                 185                 190

Leu Glu Lys Leu Ser Phe Glu Glu Met Leu Glu Leu Ala Ala Val Gly
                    195                 200                 205

Ser Lys Val Leu Val Leu Arg Ser Val Glu Tyr Ala Arg Ala Phe Asn
            210                 215                 220

Val Pro Pro Arg Val Arg Ser Ser Tyr Ser Asp Asp Pro Gly Thr Leu
225                 230                 235                 240

Ile Ala Gly Ser Met Glu Asp Ile Pro Val Glu Ala Val Leu Thr
                    245                 250                 255

Gly Val Ala Thr Asp Lys Ser Glu Ala Lys Val Thr Val Leu Gly Ile
                    260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
            290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                    325                 330                 335

Asn Val Leu Tyr Asp Asp Gln Val Gly Lys Val Ser Leu Ala Gly Ala
                    340                 345                 350

Gly Met Lys Ser His Pro Gly Val Thr Ala Glu Phe Met Glu Ala Leu
            355                 360                 365

Arg Asp Val Asn Val Asp Ile Glu Leu Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                    405                 410                 415

Ala Gly Thr Gly Arg
            420

<210> SEQ ID NO 27
<211> LENGTH: 1266
<212> TYPE: DNA
<213> ORGANISM: Corynebacterium glutamicum

<400> SEQUENCE: 27
gtggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
```

```
ccgccagctc gtgaaatgga tatgctcctg actgctggtg agcgtatttc taacgctctc      240
gtcgccatgg ctattgagtc ccttggcgca gaagcccaat ctttcacggg ctctcaggct      300
ggtgtgctca ccaccgagcg ccacggaaac gcacgcattg ttgatgtcac tccaggtcgt      360
gtgcgtgaag cactcgatga gggcaagatc tgcattgttg ctggtttcca gggtgttaat      420
aaagaaaccc gcgatgtcac cacgttgggt cgtggtggtt ctgacaccac tgcaggtgcg      480
ttggcagctg ctttgaacgc tgatgtgtgt gagatttact cggacgttga cggtgtgtat      540
accgctgacc cgcgcatcgt tcctaatgca cagaagctgg aaaagctcag cttcgaagaa      600
atgctggaac ttgctgctgt tggctccaag attttggtgc tgcgcagtgt tgaatacgct      660
cgtgcattca atgtgccact tcgcgtacgc tcgtcttata gtaatgatcc cggcactttg      720
attgccggct ctatggagga tattcctgtg aagaagcag tccttaccgg tgtcgcaacc       780
gacaagtccg aagccaaagt aaccgttctg ggtatttccg ataagccagg cgaggctgcg      840
aaggttttcc gtcgcgttggc tgatgcagaa atcaacattg acatggttct gcagaacgtc      900
tcttctgtag aagacggcac caccgacatc accttcacct gccctcgttc cgacggccgc      960
cgcgcgatgg agatcttgaa gaagcttcag gttcagggca actggaccag tgtgctttac     1020
aacgaccagg tcgcaaagt ctccctcgtg ggtgctggca tgaagtctca cccaggtgtt      1080
accgcagagt tcatggaagc tctgcgcgat gtcaacgtga acatcgaatt gatttccacc     1140
tctgagattc gtatttccgt gctgatccgt gaagatgatc tggatgctgc tgcacgtgca     1200
ttgcatgagc agttccagct gggcggcgaa gacgaagccg tcgtttatgc aggcaccgga     1260
cgctaa                                                                1266
```

<210> SEQ ID NO 28
<211> LENGTH: 421
<212> TYPE: PRT
<213> ORGANISM: Corynebacterium glutamicum

<400> SEQUENCE: 28

```
Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Gly Ala
145                 150                 155                 160

Leu Ala Ala Ala Leu Asn Ala Asp Val Cys Glu Ile Tyr Ser Asp Val
                165                 170                 175
```

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Ser Val Leu Tyr Asn Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 29
<211> LENGTH: 1266
<212> TYPE: DNA
<213> ORGANISM: Corynebacterium glutamicum

<400> SEQUENCE: 29
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttcacggg ctctcaggct      300 ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt ggctccaagc attttggtgc tgcgcagtgt tgaatacgct     660
cgtgcattca atgtgccact tcgcgtacgc tcgtcttata gtaatgatcc cggcactttg     720

```
attgccggct ctatggagga tattcctgtg gaagaagcag tccttaccgg tgtcgcaacc    780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgcag aagacggcac caccgacatc accttcacct gccctcgttc cgacggccgc    960
cgcgcgatgg agatcttgaa gaagcttcag gttcagggca actggaccaa tgtgctttac   1020
gacgaccagg tcggcaaagt ctccctcgtg ggtgctggct gaagtctca cccaggtgtt   1080
accgcagagt tcatggaagc tctgcgcgat gtcaacgtga acatcgaatt gatttccacc   1140
tctgagattc gtatttctgt gctgatccgt gaagatgatc tggatgctgc tgcacgtgca   1200
ttgcatgagc agttccagct gggcggcgaa gacgaagccg tcgtttatgc aggcaccgga   1260
cgctaa                                                              1266
```

<210> SEQ ID NO 30
<211> LENGTH: 421
<212> TYPE: PRT
<213> ORGANISM: Corynebacterium glutamicum

<400> SEQUENCE: 30

```
Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270
```

```
Ser Asp Lys Pro Gly Glu Ala Ala Lys Val Phe Arg Ala Leu Ala Asp
    275                 280                 285

Ala Glu Ile Asn Ile Asp Met Val Leu Gln Asn Val Ser Ser Ala Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
            325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
            405                 410                 415

Ala Gly Thr Gly Arg
            420

<210> SEQ ID NO 31
<211> LENGTH: 1266
<212> TYPE: DNA
<213> ORGANISM: Corynebacterium glutamicum

<400> SEQUENCE: 31
gtggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttttcacgg gctctcaggc     300 tggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgtttggg cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgctttca atgtgccact tcgcgtacgc tcgtcttata gtaatgatcc cggcgctttg     720
attgccggct ctatggagga tattcctgtg aagaagcag tccttaccgg tgtcgcaacc     780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
```

```
ttgcatgagc agttccagct gggcggcgaa gacgaagccg tcgtttatgc aggcaccgga    1260
cgctaa                                                                1266
```

<210> SEQ ID NO 32
<211> LENGTH: 421
<212> TYPE: PRT
<213> ORGANISM: Corynebacterium glutamicum

<400> SEQUENCE: 32

```
Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Val Asn Pro Val Pro Pro Ala Arg
50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Ala Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
```

```
                355                 360                 365
Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 33
<211> LENGTH: 1266
<212> TYPE: DNA
<213> ORGANISM: Corynebacterium glutamicum

<400> SEQUENCE: 33
gtggccctgg tcgtacagaa atatggcggt tcctcgcttg agagtgcgga acgcattaga      60
gacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat ctttcacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag attttggtgc tgcgcagtgt tgaatacgct     660
cgtgcattca atgtgccact tcgcgtacgc tcgtctttata gtaatgatcc cggcactttg     720
attgccggct ctatggagga tattcctgtg aagaagcag tccttaccgg tgtcgcaacc     780
gacaagtccg aagccaaagt aaccgttctg ggtatttccg ataagccagg cggggctgtg     840
aaggttttcc gtgcgttggc tgatgcagaa atcaacattg acatggttct gcagaacgtc     900
tcttctgtag aagacggcac caccgacatc accttcacct gccctcgttc cgacggccgc     960
cgcgcgatgg agatcttgaa gaagcttcag gttcagggca actggaccaa tgtgctttac    1020
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt ggagatgatc tggatgctgc tgcacgtgca    1200
ttgcatgagc agttccagct gggcggcgaa gacgaagccg tcgtttatgc aggcaccgga    1260
cgctaa                                                                1266

<210> SEQ ID NO 34
<211> LENGTH: 421
<212> TYPE: PRT
<213> ORGANISM: Corynebacterium glutamicum

<400> SEQUENCE: 34

Val Ala Leu Val Val Gln Lys Tyr Gly Gly Ser Ser Leu Glu Ser Ala
1               5                   10                  15

Glu Arg Ile Arg Asp Val Ala Glu Arg Ile Val Ala Thr Lys Lys Ala
            20                  25                  30
```

```
Gly Asn Asp Val Val Val Cys Ser Ala Met Gly Asp Thr Thr Asp
         35                  40                  45

Glu Leu Leu Glu Leu Ala Ala Val Asn Pro Val Pro Pro Ala Arg
 50                  55                  60

Glu Met Asp Met Leu Leu Thr Ala Gly Glu Arg Ile Ser Asn Ala Leu
 65                  70                  75                  80

Val Ala Met Ala Ile Glu Ser Leu Gly Ala Glu Ala Gln Ser Phe Thr
                 85                  90                  95

Gly Ser Gln Ala Gly Val Leu Thr Thr Glu Arg His Gly Asn Ala Arg
                100                 105                 110

Ile Val Asp Val Thr Pro Gly Arg Val Arg Glu Ala Leu Asp Glu Gly
                115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
                180                 185                 190

Leu Glu Lys Leu Ser Phe Glu Glu Met Leu Glu Leu Ala Ala Val Gly
                195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Gly Ala Val Lys Val Phe Arg Ala Leu Ala Asp
                275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
                355                 360                 365

Arg Asp Val Asn Val Asn Ile Glu Leu Ile Ser Thr Ser Glu Ile Arg
                370                 375                 380

Ile Ser Val Leu Ile Arg Gly Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
                420
```

METHOD FOR PRODUCING VECTORS CONTAINING A GENE CODING FOR AN ENZYME HAVING REDUCED OR DEACTIVATED FEEDBACK INHIBITION AND THE USE THEREOF FOR PRODUCING AMINO ACIDS AND NUCLEOTIDES

BACKGROUND OF THE INVENTION

The invention relates to a method for producing vectors containing a gene coding for an enzyme having reduced or deactivated feedback inhibition and to the use thereof for producing amino acids and nucleotides Amino acids are used in human medicine, in the pharmaceutical industry, the food industry, and particularly in animal nutrition. Amino acids are known to be produced by the fermentation of strains of coryneform bacteria, in particular *Corynebacterium glutamicum*, and of enterobacteria, in particular *Escherichia coli*. Due to their great significance, efforts are continually underway to improve production methods. Improvements to the process can relate to measures concerning fermentation techniques, such as stirring and the supply of oxygen, or to the composition of the nutrient media, such as the sugar concentration during fermentation or processing into product form by ion exchange chromatography, for example, or to the intrinsic performance characteristics of the microorganism itself.

Mutagenesis, selection, and mutant selection methods are employed to improve the performance characteristics of these microorganisms. In this way, strains are obtained that are resistant to antimetabolites or are auxotrophic for regulatorily significant metabolites and produce amino acids. Likewise, recombinant DNA methods are used to improve strains of L-amino acid producing strains by amplifying individual amino acid biosynthesis genes and analyzing the effect on amino acid production.

The synthesis of amino acids in microorganism takes place by way of synthesis pathways, which are referred to as amino acid biosynthesis pathways, amino acid synthesis pathways, or synthesis pathways. These synthesis pathways are composed of individual steps, in which the amino acid is synthesized from precursors. These precursors are provided in the central metabolism. They include, for example, pyruvate, alpha-ketoglutarate, oxaloacetate, pentose phosphate, acetyl-CoA, erythrose phosphate, phosphoenolpyruvate or phosphoglycerate. Moreover NADPH2, NH4+ and reduced tetrahydrofolate are required to synthesize amino acids from precursors using the synthesis pathways. The synthesis of amino acids from precursors using synthesis pathways in coryneform bacteria and enterobacteria is known to those skilled in the art. This relates to the amino acids L-alanine, L-valine, L-leucine, L-asparagine, L-aspartate, L-lysine, L-methionine, L-threonine, L-isoleucine, L-histidine, L-glutamate, L-glutamine, proline, glycine, L-arginine, L-tryptophan, L-tyrosine, L-phenylalanine, L-serine and L-cysteine. The synthesis of amino acids has been studied particularly well in *Escherichia coli* and *Corynebacterium glutamicum*.

The synthesis pathways consist of a series of reactions catalyzed by enzymes and are subject to strict regulations. Particularly strict regulation is achieved by feedback-resistant enzymes. In wild type strains, strict regulating mechanisms prevent the production of metabolic products, such as amino acids, beyond the subsistence level needed and the delivery thereof to the medium. From a manufacturer's view, the construction of strains overproducing organic-chemical compounds therefore entails the need to overcome these metabolic regulations. These feedback-resistant enzymes preferably catalyze input reactions of the synthesis pathways or branch points on the synthesis pathways. The regulation often takes place via the end product of the synthesis pathway, which is to say the amino acids L-alanine, L-valine, L-leucine, L-asparagine, L-aspartate, L-lysine, L-methionine, L-threonine, L-isoleucine, L-histidine, L-glutamate, L-glutamine, proline, glycine, L-arginine, L-tryptophan, L-tyrosine, L-phenylalanine, L-serine and L-cysteine.

Intermediates can also intervene in a regulating manner, such as O-acetylserine, O-acetylhomoserine, O-succinylserine, O-succinylhomoserine or adenosylmethionine. Regulation is such that, at an increased concentration of the listed amino acids or intermediates, the respective enzyme of the synthesis pathway, or the feedback-resistant enzymes of the synthesis pathway, are inhibited.

Examples of enzymes of synthesis pathways according to the prior art, formed in the cell by feedback-controlled formation, and the genes coding for the same, are shown in Table 1. In addition, the EC numbers are indicated, which characterize the respective reaction with respect to the substrates and products of the mechanism of the key reaction. In addition, the accession numbers for sequences of the regulated feedback-resistant enzymes of the wild type of *E. coli* and *C. glutamicum* are indicated. The nucleotide sequences of these genes and the coded polypeptide sequences are stored in public databases. For *C. glutamicum*, for example, in the National Center for Biotechnology Information (NCBI) database of the National Library of Medicine (Bethesda, Md., USA) under accession numbers NC_003450.2 and BX927148.1 to BX927157.1. The nucleotide sequences of these genes and the coded polypeptide sequences of *E. coli* have been described by Blattner et al. (Science 277: 1453-1462 (1997)) and stored in the National Center for Biotechnology Information (NCBI) database of the National Library of Medicine (Bethesda, Md., USA) under accession number NC_000913.2. Access is also possible via the database UniProtKB/Swiss-Prot European Molecular Biology Laboratory, Heidelberg.

TABLE 1

Examples of feedback-inhibited enzymes, the enzyme classification numbers characterizing the same, the genes coding for the same, and the exemplary accession numbers of the genes for *E. coli* and *C. glutamicum*

| Enzyme | EC Number | Gene | Accession number *E. coli* | Accession number *C. glutamicum* |
|---|---|---|---|---|
| 2-isopropylmalate synthase | EC 2.3.3.13 | leuA | EG11226 | YP_224548 |
| Acetohydoxy acid synthase | EC 2.2.1.6 | ilvN | EG10502 | YP_225560.1 |
| Acetohydoxy acid synthase | EC 2.2.1.6 | ilvB | EG10494 | YP_225561.1 |
| Acetohydoxy acid synthase | EC 2.2.1.6 | ilvI | EG10500 | YP_225560.1 |
| Acetohydoxy acid synthase | EC 2.2.1.6 | ilvH | EG10499 | YP_225561.1 |

TABLE 1-continued

Examples of feedback-inhibited enzymes, the enzyme classification numbers characterizing the same, the genes coding for the same, and the exemplary accession numbers of the genes for *E. coli* and *C. glutamicum*

| Enzyme | EC Number | Gene | Accession number E. coli | Accession number C. glutamicum |
|---|---|---|---|---|
| Acetylglutamate synthase | EC 2.3.1.1 | argA | EG10063 | YP_225682.1 |
| Anthranilate synthase | EC 4.1.3.27 | trpD | EG11027 | YP_227281.1 |
| Anthranilate synthase | EC 4.1.3.27 | trpE | EG11028 | YP_227280.1 |
| Asparagine synthetase B | EC 6.3.5.4 | asnB | NP_415200.1 | NC_006958.1 |
| Aspartate transcarbamylase | EC 2.1.3.2 | pyrB | NP_418666 | Q8NQ38 |
| Aspartate transcarbamylase | EC 2.1.3.2 | pyrI | NP_418665.1 | Q8NQ38 |
| Aspartate kinase | EC 2.7.2.4 | lysC | EG10550 | P26512.2 |
| Aspartate kinase | EC 2.7.2.4 | metL | EG10590 | P26512.2 |
| Aspartate kinase | EC 2.7.2.4 | thrA | EG10998 | P26512.2 |
| ATP-phosphoribosyl transferase | EC 2.4.2.17 | hisG | EG10449 | Q9Z472.2 |
| Carbamoyl phosphate synthetase | EC 6.3.5.5 | carA | EG10134 | Q8NSR1.1 |
| Carbamoyl phosphate synthetase | EC 6.3.5.5 | carB | NP_414574.1 | P58939.1 |
| Chorismate mutase I | EC 5.4.99.5 | tyrA | EG11039 | BAB98246.1 |
| Chorismate mutase 11 | EC 5.4.99.5 | pheA | EG10707 | YP_227138.1 |
| Cysteine synthase | EC 2.5.1.47 | cysK | NP_416909.1 | CBV01938.1 |
| Cysteine synthase | EC 2.5.1.47 | cysM | NP_416916.1 | CBF99279.1 |
| D-3-phosphoglycerate dehydrogenase | EC 1.1.1.95 | serA | NP_417388.1 | AEA48241.1 |
| 3-deoxy-D-arabino-heptulosonate-7-phosphate synthase | EC 4.1.2.15 | aroG | NP_415275.1 | CAC25920.1 |
| Dihydrodipicolinate synthase | EC 4.2.1.52 | dapA | NP_416973.1 | CAA37940.1 |
| Glutamate dehydrogenase | EC 1.4.1.4 | gdh | NP_416275.1 | NP_601679.1 |
| Glutamate synthase | EC 1.4.1.13 | gltB | NP_417679.2 | YP_224481.1 |
| Glutamate synthase | EC 1.4.1.13 | gltD | NP_417680.1 | YP_226992.1 |
| Glutamine synthetase | EC 6.3.1.2 | glnA | NP_418306.1 | YP_226471.1 |
| Glutamyl kinase | EC 2.7.2.11 | proB | NP_414777.1 | YP_226601.1 |
| Homocysteine transmethylase | EC 2.1.1.14 | metE | NP_418273.1 | CAF19845.1 |
| Homoserine O-aceyltransferase | EC 2.3.1.46 | metX | NP_417417.1 | NP_600817.1 |
| Homoserine O-succinyltransferase | EC 2.3.1.46 | metA | NP_418437.1 | YP_225473.1 |
| Homoserine dehydrogenase | EC 1.1.1.3 | metL | EG10590 | CAF19887.1 |
| Homoserine dehydrogenase | EC 1.1.1.3 | thrA | EG10998 | NP_414543.1 |
| Methionine synthase | EC 2.1.1.13 | metH | NP_418443.1 | NP_600723.1 |
| Phosphoribosylpyrophosphate synthetase | EC 2.7.6.1 | prs | NP_415725.1 | YP_225235.1 |
| Prephenate dehydrogenase I | EC 1.3.1.12 | pheA | NP_417090.1 | CAF20922.1 |
| Prephenate dehydrogenase II | EC 1.3.1.12 | tyrA | EG11039 | YP_227138.1 |
| Pyrroline-5-carboxylate reductase | EC 1.5.1.2 | proC | NP_414920.1 | NP_599858.1 |
| Ribose 1,5-bisphosphokinase | EC 2.7.4.23 | phnN | NP_418518.1 | NP_600170 |
| Serine acetyl(succinyl)transferase | EC 2.3.1.30 | cysE | NP_418064.1 | NP_601761.1 |
| Threonine ammonia-lyase | EC 4.3.1.19 | ilvA | NP_418220.1 | NP_601328.2 |
| Tyrosine aminotransferase | EC 2.6.1.57 | tyrB | NP_418478.1 | NP_599471.2 |

Proceeding from the wild form of the feedback-regulated enzymes mentioned in Table 1 by way of example, there is a need to achieve deregulation of the enzyme activity so as to improve the production of target compounds, such as amino acids, nucleotides, amino acid derivatives or intermediates of the synthesis pathways.

It is known that such feedback-resistant enzymes, the regulation of which has been eliminated so as to contribute to improving the performance capability of microorganisms, is important, and feedback-resistant alleles carrying mutations as compared to the wild type have been described. For example, it is described in DE102008040352A1 and EP000002147972A1 that alleles of aroG coding for 3-deoxy-D-arabino-heptulosonate-7-phosphate synthase led to improved formation of tryptophan. Moreover, a recombinant, L-lysine-producing bacterium is known, for example, containing an lysC allele with feedback-resistant aspartate kinase (EP0381527A1). In addition, a recombinant, L-phenylalanine-producing bacterium with feedback-resistant prephenate dehydrogenase is described (EP088424A2). Moreover, a leuA allele is described, which codes for a mutated isopropylmalate synthase and a microorganism producing L-leucine (EP000001568776B1). A mutant acetolactate synthase having a mutation in the IlvN subunit and a microorganism overproducing L-valine are described in EP07017918.9. An allele is also described for the enzyme acetylglutamate synthase, which is feedback-resistant to arginine as compared to the wild type enzyme, and strains that produce more L-arginine with the allele are described (U.S. Pat. No. 7,169,586 B2). Mutant alleles of phosphoribosyl pyrophosphate synthetase and methods for producing L-histidine are described (EP 1529839 A1). It is also known that L-histidine biosynthetic enzymes encoded by hisG and hisBHAFI are inhibited by L-histidine, and therefore the ability to produce L-histidine can also be effectively enhanced by introducing a mutation conferring resistance to feedback inhibition into ATP phosphoribosyl transferase (Russian patents nos. 2003677 and 2119536). Improved arginine production was achieved when the enzyme used was carbamoyl phosphate synthetase (EP000001026247A). The introduction of a cysE allele coding for a serine O-acetyltransferase having reduced feedback inhibition through L-cysteine also increased the production of cysteine (US6218168B1; Nakamori et al., 1998, Appl. Env. Microbiol. 64: 1607-1611; Takagi et al., 1999, FEBS Lett. 452: 323-327). A feedback-resistant CysE enzyme substantially decouples the production of O-acetyl-L-serine, the immediate precursor of L-cysteine, from the L-cysteine level of the cell.

Mutagenesis, selection, and mutant selection methods are employed to eliminate the control mechanisms and improve the performance characteristics of these microorganisms. In this way strains are obtained, which are resistant to antimetabolites, such as alpha-amino-beta-hydroxyvaleric acid (AHV), an analog of threonine, or are auxotrophic for regulatorily significant metabolites, and produce amino acids, such as L-threonine. Resistance to 5-methyl-DL-tryptophan (5-MT), a tryptophan analog, is characteristic of a strain producing L-tryptophan, for example (DE 102008040352 A1). In addition, strains that were resistant to 4-aza-D,L-leucine or 3-hydroxy-D,L-leucine, β-2-thienyl-alanine, 3-hydroxyleucine, 4-azaleucine and 5,5,5-trifluoroleucine included a feedback-resistant isopropylmalate dehydrogenase (EP 1568776A2, EP 1067191 A2). Strains are described having acetolactate synthases which exhibit reduced feedback inhibition through the use of the inhibitors sulfonylurea and imidazolinone (CA 2663711 A1). It has also been possible to obtain strains with argA alleles that are suitable for producing L-arginine by selecting slowly growing mutants (U.S. Pat. No. 7,169,586 B2). Likewise, arginine producers were obtained via the resistance-conferring substances 5-azauracil, 6-azauracil, 2-thiouracil, 5-fluorouracil, 5-bromouracil, 5-azacytosine, 6-azacytosine, arginine hydroxamate, 2-thiouracil and 6-azauracil (Japanese patent 49-126819). By utilizing analogs of pyrimidine, such as azidothymidine or azidodeoxyurldine, it is possible to obtain strains in which feedback-resistant enzymes, such as the aspartate transcarbamoylase of the shared synthesis pathway of L-histidine, purine and pyrimidine are mutated (U.S. Pat. No. 5,213,972). By utilizing analogs of lysine, such as S-(2-aminoethyl)-cysteine, it has been possible to obtain lysC alleles, or by utilizing analogs of methionine, such as alpha-methylmethionine, ethionine, norleucine, N-acetyl-norleucine, S-trifluoromethylhomocysteine, 2-amino-5-heprenoit acid, selenomethionine, methionine sulfoximine, methoxine, 1-aminocyclopentane carboxylic acid, it has been possible to obtain strains with alleles that accumulate L-methionine at an increased level (EP 1745138 B1). Through the use of 1,2,4-triazole-D-alanine, it has been possible to eliminate the feedback inhibition of the HisG allele hisG13 and thereby obtain strains having enhanced performance characteristics (Mizukami T et al., Biosci Biotechnol Biochem. 1994 April, 58(4):635-8).

A major drawback in the existing production of enzymes having reduced feedback resistance is the use of analogs, such as alpha-amino-beta-hydroxyvaleric acid, 5-methyl-DL-tryptophan, 4-aza-D,L-leucine or 3-hydroxy-D,L-leucine, β-2-thienylalanine, 3-hydroxyleucine, 4-azaleucine, 5,5,5-trifluoroleucine, sulfonylurea, imidazolinone, 5-azauracil, 6-azauracil, 2-thiouracil, 5-fluorouracil, 5-bromouracil, 5-azacytosine, 6-azacytosine, arginine hydroxamate, 2-thiouracil, 6-azauracil, azidothymidine, azidodeoxyuridine, S-(2-aminoethyl)-cysteine, alpha-methyl-methionine, ethionine, norleucine, N-acetylnorleucine, S-trifluoromethylhomocysteine, 2-amino-5-heprenoit acid, selenomethionine, methionine sulfoximine, methoxine, 1-aminocyclopentane carboxylic acid, 1,2,4,-triazole-D-alanine and the isolation of mutants resistant to such analogs. Another major drawback of existing methods for producing feedback-resistant enzymes, and of the use thereof to enhance the performance capability of the microorganisms, is that many strains must be tested for enhanced performance capability following undirected mutagenesis and the use of analogs, since resistance to analogs can have a wide variety of causes, such as improved decomposition of the analog, or improved export of the analog, which can feign a feedback resistance and results in no new feedback-resistant enzymes being produced, and no strain having enhanced performance capability being present. Existing techniques for isolating the targeted production of feedback-resistant enzymes, which are directed to enhancing the performance capability of microorganisms for the production of amino acids, can therefore achieve the object only partially, incompletely or not at all.

SUMMARY OF THE INVENTION

It is therefore the object of the invention to create a method for producing vectors containing a gene coding for an enzyme having reduced or deactivated feedback inhibition, which allows feedback-resistant enzymes, or enzymes having reduced inhibition as compared to the wild type, and the deoxyribonucleic acid coding therefor, to be provided more reliably, more quickly, and better. Moreover, feedback-resistant enzymes, or enzymes having reduced inhibition, and the deoxyribonucleic acids coding for them, are to be provided.

The method according to the invention now makes it possible to provide or obtain feedback-resistant enzymes, or enzymes having reduced inhibition as compared to the wild type, and the deoxyribonucleic acid coding therefor and vectors containing this deoxyribonucleic acid. The method is more accurate, more reliable and faster than the methods according to the prior art, since the procedure does not feign feedback resistance, or a reduction in feedback resistance, but the same is established in direct causal relation with the methods that are carried out.

DETAILED DESCRIPTION OF THE PREFERRED EMBODIMENTS

The invention will be explained hereinafter in the general form thereof.

In a first step, the feedback-sensitive gene of the wild type of a microorganism, for example of a bacterium or a yeast, is mutagenized in vitro as the starting organism and ligated to a vector.

As a result of the ligation approach, a microorganism is transformed, and a vector gene bank is obtained. The microorganism used for transformation is one that contains a metabolite sensor, which results in synthesis of a fluorescent protein at an increased metabolite concentration.

In a subsequent step, microorganisms having the highest fluorescence are selected, and the vectors thereof are isolated. It is also possible to select microorganisms having fluorescence induced by the metabolite sensor, which is increased as compared to the starting organism containing the wild-type gene.

These method steps can be used to ascertain which mutant produces the highest, or increased, production of the desired product.

The vectors that are isolated according to this method contain genes coding for enzymes having reduced or deactivated feedback inhibition.

These genes contained in the vectors, which code for enzymes having reduced or deactivated feedback inhibition, can be used in methods known to a person skilled in the art for producing amino acids, nucleotides or intermediates. By way of example, the following method steps, which are known to a person skilled in the art, can be carried out for this purpose:

The genes coding for enzymes having reduced or deactivated feedback inhibition can be introduced on the vector into the production strain, giving the same the ability to better produce the desired product.

As an alternative, the genes coding for enzymes having reduced or deactivated feedback inhibition can be inserted in vectors that are already used to produce the desired product and result in an additional increase in the product formation.

In a further embodiment, the genes coding for enzymes having reduced or deactivated feedback inhibition can be introduced into the chromosome of the production strain, giving this the ability to better produce the desired product.

A feedback-sensitive gene within the meaning of the invention shall be understood to mean a deoxyribonucleic acid coding for an enzyme in which feedback inhibition is caused. It does not matter whether the feedback inhibition is the result of the product that is formed or of an intermediate created during production.

The term "wild type" within the meaning of the invention shall be understood to mean a gene, or a gene from a strain, which has not yet been modified by way of the method according to the invention, or which already underwent a modification according to the invention, and the coding enzyme activity of which is to be further increased, which is to say which is to be used as the starting gene for the method according to the invention. This can be a naturally occurring gene, or a gene from a strain that was genetically modified, which is used as the starting material for the mutagenesis that is carried out according to the invention.

The mutagenization can preferably be carried out by way of undirected methods which are known from the prior art, such as by way of a faulty polymerase chain reaction, for example.

The starting organism from which the gene to be modified is procured can be any arbitrary microorganism containing a gene for a protein subject to feedback regulation or feedback inhibition, for example a bacterium, such as a *Corynebacterium* or an *Enterobacterium*, or a yeast, such as *Saccharomyces cerevisiae*. In particular *Corynebacterium glutamicum* or *E. coli* can be used as the starting organism.

By way of example, and without limitation, the organisms mentioned in Table 1, and the genes and enzymes thereof, can be used for modification according to the invention.

According to the invention, the amino acid sequences of feedback-controlled enzymes disclosed in Table 1, and the nucleic acid sequences of the genes coding for the same, serving as starting materials for the method according to the invention, also comprise such sequences that exhibit homology (at the amino acid level) or identity (at the nucleic acid level, exclusive of the natural degeneration) of greater than 70%, preferably 80%, more preferably 85% (based on the nucleic acid sequence) or 90% (also based on the polypeptides), preferably greater than 91%, 92%, 93% or 94%, more preferably greater than 95% or 96%, and particularly preferably greater than 97%, 98% or 99% (based on both types of sequences) with one of these sequences, as long as the mode of action or function and purpose of such a sequence are preserved. The term "homology" (or identity) as used herein can be defined by the equation $H (\%)=[1-V/X]\times 100$, where H denotes homology, X is the total number of nucleobases/amino acids of the comparison sequence, and V is the number of different nucleobases/amino acids of the sequence to be examined based on the comparison sequence. In any case, the term 'nucleic acid sequences' coding for polypeptides encompasses all sequences that appear possible according to the proviso of degeneration of the genetic code. The same also applies to all other possible genes or enzymes that are to be modified according to the invention and not listed in Table 1.

The identity, in percent, with the amino acid sequences indicated in this description by the accession number (Accession No.) in Table 1 can be readily ascertained by a person skilled in the art using methods known in the prior art. A suitable program that can be used according to the invention is BLASTP (Altschul et al. 1997. Gapped BLAST and PSI-BLAST: a new generation of protein database search programs. Nucleic Acids Res. 25(17): 3389-3402).

According to the invention, the nucleic acid sequences of the gene coding for feedback-sensitive enzymes disclosed in Table 1 also comprise nucleic acid sequences hybridized with those listed. A person skilled in the art can find instructions on hybridization, among other things, in "The DIG System Users Guide for Filter Hybridization" from Boehringer Mannheim GmbH (Mannheim, Germany, 1993) and in Liebl et al. (International Journal of Systematic Bacteriology 41: 255-260 (1991)). The hybridization takes place under stringent conditions, which is to say only hybrids are formed, in which the probe, for example the nucleotide sequence complementary to the gene, and the target sequence, which is to say the polynucleotides treated with the probe, are at least 70% identical. It is known that the stringency of the hybridization process, including the washing steps, is influenced or determined by varying the buffer composition, the temperature and the salt concentration. The hybridization reaction is generally carried out at relatively low stringency in comparison with the washing steps (Hybaid Hybridisation Guide, Hybaid Limited, Teddington, UK, 1996). For example, a buffer corresponding to 5×SCC buffer at a temperature of approximately 50° C. to 68° C. can be used for the hybridization reaction. Probes can also hybridize with polynucleotides having an identity lower than 70% with the sequence of the probe. Such hybrids are less stable and are removed by washing under stringent conditions. This can be achieved, for example, by lowering the salt concentration to 2×SCC, and optionally subsequently 0.5× SCC (The DIG System User's Guide for Filter Hybridisation, Boehringer Mannheim, Mannheim, Germany, 1995), wherein the temperature is set to approximately 50° C. to 68° C., approximately 52° C. to 68° C., approximately 54° C. to 68° C., approximately 56° C. to 68° C., approximately 58° C. to 68° C., approximately 60° C. to 68° C., approximately 62° C. to 68° C., approximately 64° C. to 68° C., or approximately 66° C. to 68° C. The washing steps are preferably carried out at temperatures of approximately 62° C. to 68° C., preferably 64° C. to 68° C., or approximately 66° C. to 68° C., and particularly preferably 66'C to 68° C. Optionally, it is possible to lower the salt concentration to a concentration corresponding to 0.2×SCC or 0.1×SSC. By incrementally increasing the hybridization temperature in steps of approximately 1 to 2° C. from 50° C. to 68° C., it is possible to isolate polynucleotide fragments coding for feedback-sensitive enzymes, which have, for example, at least 70%, or at least 80%, or at least 90% to 95%, or at least 96% to 98%, or at least 99% identity with the sequence of the probe that is used. Further hybridization instructions are available on the market in the form of so-called kits (such as DIG Easy Hyb from Roche Diagnostics GmbH, Mannheim, Germany, Catalog No. 1603558). Analogously, it is also possible to use other amino acid sequences not mentioned in Table 1, and genes coding for the same, in hybridized form as starting materials for the feedback-resistant genes modified according to the invention.

All known plasmid bodies, transposons, insertion elements or phages can be used as raw materials for the vectors, in which the mutagenized genes were inserted. By way of example, and without limitation, vectors can be used that are derived from pACYC184 (Bartolome et al.; Gene 102, 75-78 (1991)), or pTrc99A (Amann at al.: Gene 69: 301-315 (1988)) or pSC101 (Vocke and Bastia, Proceedings of the National Academy of Sciences USA 80 (21): 6557-6561 (1983)). Such genetic systems are described in the patent specifications of U.S. Pat. No. 4,822,738, U.S. Pat. No. 5,804,414 and U.S. Pat. No. 5,804,414, for example. Similarly, it is also possible to use vectors such as pZ1, pXZ10142, pEKEx2, pEKEx3, or pEC-t19mob2 (cited in "Handbook of *Corynebacterium glutamicum*" (publisher: L. Eggeling and M. Bott)), which are used for the method according to the invention.

Known metabolite sensors, such as pSenLys, pSenArg, pSenSer, pSenOAS or pJC1-lrp-bmF-eyfp, can be used as metabolite sensors. The metabolite sensor includes a gene sequence coding for an autofluorescent protein, wherein the expression of the autofluorescent protein is dependent on the intracellular concentration of a particular metabolite. The expression of the gene sequence coding for the autofluorescent protein is controlled as a function of the intracellular concentration of the particular metabolite at the transcription level. Depending on the intracellular concentration of the respective metabolite, more or less mRNA is therefore produced, which can be translated by the ribosomes, forming the autofluorescent protein.

The microorganism used for transformation can be any arbitrary microorganism. Bacteria, yeasts or enterobacteria, such as *E. coli, Corynebacterium glutamicum* or *Saccharomyces cerevisiae*, can be mentioned by way of example. The microorganism used for transformation is a microorganism that contains a metabolite sensor, which results in synthesis of a fluorescent protein at a metabolite concentration that is higher than the metabolite concentration present in the starting organism.

Deposit of the following biological material (i.e., plasmids containing named metabolite sensor(s)) has been made at Leibuiz Institute DSMZ-German Collection of Microorganisms and Cell Cultures, Inhoffenstraβe 7B, 38124 Braunschweig, GERMANY, a depository accredited according to the Budapest Treaty, in a manner by which such biological material is readily and irrevocably available to the public: pSenArg (Accession Number DSM 32346) deposited on Jul. 22, 2016; pSenLys (Accession number 32347) deposited on Jul. 22, 2016; pSenSer (Accession number 32351) deposited on Jul. 22, 2016; and pSenOAS (Accession number 32350) deposited on Jul. 22, 2016.

For transformation, the vectors containing genes that code for enzymes having reduced or deactivated feedback inhibition can be introduced. These can be obtained directly from selection by way of metabolite sensors.

The embodiment, in which the genes coding for enzymes having reduced or deactivated feedback inhibition can be introduced in other vectors that are already used to produce the desired product, can involve vectors that are already used to produce the desired product and that already contain genes that enhance the production characteristic of the microorganism used for production.

In the embodiment, in which the genes coding for enzymes having reduced or deactivated feedback inhibition can be introduced into the chromosome of the production strain, which is then given the ability to better produce the desired product, the insertion can take place at any arbitrary position on the chromosome according to methods known to a person skilled in the art.

The production strain used can be any one of the strains used in biotechnology, in which plasmids are introduced in the mutagenized genes coding for feedback-resistant enzymes, or enzymes having reduced feedback sensitivity. Coryneform bacteria, enterobacteria or yeasts, such as *E. coli, Corynebacterium glutamicum* or *Saccharomyces cerevisiae*, can be mentioned by way of example.

The method according to the invention is generally used to provide any enzyme that is of interest and the deoxyribonucleic acid coding therefor, the inhibition of which is either completely eliminated or, at a minimum, reduced.

By way of example, and without limitation, the enzymes mentioned in Table 1 and every deoxyribonucleic acid coding for them can be mentioned as materials to be modified according to the invention.

The method according to the invention can be used to enhance the production of amino acids and the derivatives thereof, nucleotides or intermediates of synthesis pathways as products compared to the prior art. The method according to the invention allows the production of amino acids and the derivatives thereof, nucleotides or Intermediates of synthesis pathways, which were not produced, or produced only to a low degree, by the corresponding microorganisms prior to the modification according to the invention.

The nucleic acids and enzymes obtained by the method according to the invention can be used for producing these desired products and are more active with respect to the function thereof. The invention will be described in more detail hereafter by way of example, and without limitation.

The invention relates to alleles of genes coding for enzymes having reduced or deactivated feedback inhibition over the wild form, which are obtained by way of metabolite sensors, wherein the wild type alleles are present in plasmid-encoded manner, which after in vitro mutagenesis are introduced in microorganisms, preferably coryneform bacteria and enterobacteria, containing the metabolite sensor, and individual cells are generated or isolated, which are recognized as cells containing an enzyme that is no longer regulated.

Metabolite sensors allow the direct detection of increased intracellular amino acid concentrations in individual cells of coryneform bacteria, such as Coryneform bacteria, and in enterobacteria, such as *Escherichia coli* (WO2011138006). Metabolite sensors moreover allow the detection of increased intracellular amino acid concentrations of L-valine, L-leucine, L-asparagine, L-lysine, L-methionine, L-threonine, L-isoleucine, L-histidine, L-glutamate, L-glutamine, proline, glycine, L-arginine, L-tryptophan, L-tyrosine, L-phenylalanine, L-serine and L-cysteine, and particularly preferably those of L-histidine, L-arginine, L-lysine and L-leucine.

Metabolic sensors also allow the detection of increased concentrations of intermediates, such as intermediates of the amino acid or nucleotide synthesis, such as O-acetylserine, O-acetylhomoserine, cystathionine, orotidine-5'-phosphate, 5-phosphoribosyl diphosphate, or inosine-5'-phosphate.

The method for producing the enzymes modified according to the invention is characterized in that the genes or alleles in which the feedback inhibition is to be eliminated or reduced are present in a vector-encoded, and preferably plasmid-encoded, manner and are not chromosomally encoded. The genes or alleles of the enzymes that are to be modified according to the invention are in particular those of the amino acid synthesis pathways leuA, ilvN, ilvB, ilvI, ilvH, argA, trpD, trpE, asnA, asnB, pyrB, pyrI, lysC, metL, thrA, hisG, carA, carB, tyrA, pheA, cysK, cysM, serA, aroG, dapA, gdh, gltB, gltD, glnA, proB, metE, metX, metA, metL, gnd, zwf, thrA, metH, prs, pheA, tyrA, proC, prs, cysE, ilvA, tyrB, preferably lysC, hisG, argB, cysE and leuA. These genes are mutagenized in vitro according to known methods. The nucleotide sequences of these genes and the coded polypeptide sequences of *C. glutamicum* are described in EP-A-1108790 and are also stored in the National Center for Biotechnology Information (prs) database of the National Library of Medicine (Bethesda, Md., USA) under accession numbers NC_003450.2 and BX927148.1 to BX927157.1. The nucleotide sequences of these genes and the coded polypeptide sequences of *E. coli* have been described by Blattner et al. (Science 277: 1453-1462 (1997)) and stored in the National Center for Biotechnology Information (NCBI) database of the National Library of Medicine (Bethesda, Md., USA) under accession number NC_000913.2. The peptides in which, according to the invention, feedback inhibition is to be reduced or deactivated also include those that are at least 90 to 95%, in particular 90%, 91%, 92%, 93%, 94%, 95%, 96%, 97%, 98% or 99% identical to the polypeptides of the enzymes LeuA, IlvN, IlvB, Ilvl, IlvH, ArgA, TrpD, TrpE, AsnA, AsnB, PyrB, PyrI, LysC, MetL, ThrA, HisG, CarA, CarB, TyrA, PheA, CysK, CysM, SerA, AroG, DapA, Gdh, GltB, Gnd, Zwf, OpcA, GltD, GlnA, ProB, MetE, MetX, MetA, MetL, Gnd, Zwf, ThrA, MetH, Prs, PheA, TyrA, ProC, Prs, CysE, IlvA, TyrB, preferably LysC, HisG, ArgB, CysE, and LeuA. The present invention also relates to the nucleotide sequences ilvN, ilvB, ilvI, ilvH, argA, trpD, trpE, asnA, asnB, pyrB, pyrI, lysC, metL, thrA, hisG, carA, carB, tyrA, pheA, cysK, cysM, serA, aroG, dapA, gdh, gltB, gftD, glnA, proB, metE, metX, metA, metL, gnd, zwf, thrA, metH, prs, pheA, tyrA, proC, prs, cysE, ilvA, tyrB, preferably lysC, hisG, argB, cysE and leuA, and such sequences exhibiting homology of at least 70%, preferably 80%, more preferably 85% (based on the nucleic acid sequence) or 90%, preferably greater than 91%, 92%, 93% or 94%, more preferably greater than 95% or 96%, and particularly preferably greater than 97%, 98% or 99% with one of these sequences, as long as the mode of action or function and purpose of such a sequence are preserved or are identical thereto.

To introduce the site-undirected mutations in the plasmid-encoded genes of the enzymes, mutagenesis, which is preferably in vitro, is carried with the aid of a faulty polymerase chain reaction (PCR) and an amplification technique. To this end, the gene to be mutated is first subjected to PCR using a polymerase, which incorrectly inserts individual nucleotides in the synthesized genes compared to the wild form as a function of the conditions of the reaction (Tindall, K. R. and T. A. Kunkel, Fidelity of DNA synthesis by the *Thermus aquaticus* DNA Polymerase. Biochemistry, 1988. 27(16): p. 6008-13). A common variant of this method includes the use of manganese(II) ions or of nucleotide analogs in the PCR batch (Cadwell R. C et al. (1992) PCR Methods Appl. 2:28-33./Leung D. W. et al. (1989) Techniques 1:11-15). These techniques for introducing mutations are referred to as "Error-prone PCR (epPCR)" (Labrou N E. Random mutagenesis methods for in vitro directed enzyme evolution. Curr Protein Pept Sci. 2010; 11:91-100). The mutations can be point mutations, for example; and it is possible to generate substitutions, deletions or insertions, for example, by way of polymerase. The mutation rate ranges between 1 and 40 mutations per 1 kb, and preferably between 1 and 5 mutations per 1 kb.

The vectors, preferably plasmids containing the mutations obtained according to the invention in genes of the enzymes, are subsequently introduced in a microorganism, such as *E. coli, C. glutamicum* or *Saccharomyces cerevisiae*, by way of transformation. The term transformation encompasses all methods for transferring polynucleotides, in particular DNA, in a desired microorganism. This includes, among other things, the use of isolated DNA during the transformation, electrotransformation or electroporation, transfer by cell contact, as in the case of conjugation, or transfer of DNA by way of particle bombardment.

During the subsequent method step of the method according to the invention, individual transformed cells in the cell suspension having an increased intracellular concentration of metabolites, as compared to the wild form of the metabolite detectable by the metabolite sensor, are identified by detection of the intracellular fluorescence. For this purpose, the cell suspension is exposed to electromagnetic radiation at that frequency which excites the autofluorescent protein of the metabolite sensor to emit light. Autofluorescent proteins are preferably proteins that are read from gene sequences which code for fluorescent proteins, for example of the Aequorea species, such as the green fluorescent protein (GFP), and variants thereof fluorescing in a different wavelength range (such as yellow fluorescent protein, YFP: blue fluorescent protein, BFP; cyan fluorescent protein, CFP) or the fluorescence of which is enhanced (enhanced GFP or EGFP, or EYFP, EBFP or ECFP). According to the invention, moreover it is also possible to use gene sequences that code for other autofluorescent proteins, such as DsRed, HcRed, AsRed, AmCyan, ZsGreen, AcGFP, ZsYellow, as they are known from BD Biosciences, Franclin Lakes, USA. The particularly preferred autofluorescent protein is EYFP or the gene coding therefor.

According to one particular embodiment of the method according to the invention, thereafter, and preferably immediately after identification of the cells, a further method step takes place, in which the identified cells are separated from the cell suspension, wherein this separation is preferably carried out by way of flow cytometry (FACS=fluorescence-activated cell sorting), most particularly preferably by way of high-throughput flow cytometry (HT-FACS=high throughput fluorescence-activated cell sorting). Details regarding the analysis of cell suspensions by way of flow cytometry can be found in Sack U, Tamok A, Rothe G (publisher): Zelluläre Diagnostik. Grundlagen, Methoden und klinische Anwendungen der Durchflusszytometrie (Cellular Diagnostics. Fundamentals, Methods and Clinical Applications of Flow Cytometry), Basel, Karger, 2007, pages 27-70, for example.

By way of the method according to the invention, it is thus possible to deliberately isolate those cells, in which feedback-resistant enzymes result in an increased intracellular concentration of a particular metabolite, in a cell suspension in which transformants are present, which contains a gene bank of plasmid-encoded enzymes.

The invention relates to use of feedback-resistant enzymes or of enzymes having reduced feedback sensitivity thus obtained, and the use of the genes coding for the same, to enhance the performance characteristics of microorganism. This is achieved in that vectors obtained by the method, for which hereinafter plasmids are listed here by way of example, and without limitation, and that code for feedback-resistant enzymes or for enzymes having reduced feedback sensitivity, are introduced directly into the microorganism. For this purpose, the plasmids are isolated according to known methods, and the microorganism to be enhanced is transformed with these plasmids. The term transformation encompasses all methods for transferring polynucleotides, in particular DNA, into a desired bacterium. This includes, among other things, the use of isolated DNA during the transformation, electrotransformation or electroporation, transfer by cell contact, as in the case of conjugation, or transfer of DNA by way of particle bombardment.

In a further embodiment, the genes that are obtained by the method and code for feedback-resistant enzymes or for enzymes having reduced feedback sensitivity are initially introduced into other plasmids, which already contain additional genes, for example, that already enhance the performance characteristic of the microorganism, or which also contain a replication origin that allows the plasmid to be replicated in the microorganism to be enhanced. Such plasmids are known to those skilled in the art, such as plasmid vectors that can be replicated in Enterobacteriaceae, such as cloning vectors derived from pA-CYC184 (Bartolomé et al.; Gene 102: 75-78 (1991)), pTrc99A (Amann et al.; Gene 69: 301-315 (1988)) or pSC101 derivatives (Vocke und Bastia; Proceedings of the National Academy of Sciences USA 80(21): 6557-6561 (1983)) or plasmids that replicate in Corynebacteria and related organisms and are listed in the Handbook of *Corynebacterium glutamicum* (eds. Eggeling and Bott), in Section 23 on pages 535-66, or in EP 1097998 B1, or the commercially available plasmids for *Bacillus* strains available from MoBiTech GmbH, Lotzestrasse 22a, 37083 Goettingen or those described for *Lactobacillus* (Wang T T, Lee B H, 1997, Crit Rev Biotechnol. Plasmids in *Lactobacillus*. 17(3):227-72) or commercially available plasmids (MoBiTech GmbH, Lotzestrasse 22a, 37083 Goettingen).

In a further embodiment, the genes that are obtained by the method and code for feedback-resistant enzymes or for enzymes having reduced feedback sensitivity are introduced into the genome of the microorganism that is to be enhanced. This is described by Reinscheid et al. (Applied and Environmental Microbiology 60, 126-132 (1994)) or in WO03/040373. In this method, the gene is cloned into a plasmid vector, which is not able to replicate in the host, the performance characteristics of which are to be enhanced. Possible vectors include, for example, pSUP301 (Simon et al., Bio/Technology 1, 784-791 (1983)), pK18mob or pK19mob (Schafer et al., Gene 145, 69-73 (1994)), pGEM-T (Promega Corporation, Madison, Wis., USA), pCR2.1-TOPO (Shuman (1994). Journal of Biological Chemistry 269:32678-84; U.S. Pat. No. 5,487,993), pCR®Blunt (Firma Invitrogen, Groningen, Netherlands; Bernard et al., Journal of Molecular Biology, 234: 534-541 (1993)), pEM1 (Schrumpf et al, 1991, Journal of Bacteriology 173:4510-4516) or pBGS8 (Spratt at al., 1986, Gene 41: 337-342). The plasmid vector coding for the feedback-resistant enzyme, or for the enzyme having reduced feedback sensitivity, and optionally including the expression and/or regulation signals, and the boundary regions of the genes, are subsequently transferred in the desired strain, the performance characteristic of which is to be enhanced by way of conjugation or transformation. The conjugation method is described in Schäfer et al. (Applied and Environmental Microbiology 60, 756-759 (1994)), for example. Methods for transformation are described in Thierbach et al. (Applied Microbiology and Biotechnology 29, 356-362 (1988)), Dunican und Shivnan (Bio/Technology 7, 1067-1070 (1989)) and Tauch et al. (FEMS Microbiology Letters 123, 343-347 (1994)), for example. Following homologous recombination by way of a "crossover" event, the resulting strain contains a copy of the heterologous gene, including the plasmid vector, at the desired gene chromosomal locus of *Corynebacterium glutamicum* or *E. coli*, for example, which was predetermined via the homologous nucleotide sequences on the plasmid. By way of a second suitable "crossover" event in the target gene or in the target sequence bringing about excision, the insertion of only the gene of the feedback-resistant enzyme, or of the enzyme having reduced feedback sensitivity, is achieved.

The invention further relates to enzymes having reduced or deactivated feedback inhibition and the genes coding therefor, which result in an increased intracellular concentration of certain metabolites, in particular amino acids such as L-valine, L-leucine, L-asparagine, L-lysine, L-methionine, L-threonine, L-isoleucine, L-histidine, L-glutamate, L-glutamine, proline, L-arginine, L-tryptophan, L-tyrosine, L-phenylalanine, L-serine and L-cysteine. The invention relates in particular to enzymes of L-lysine synthesis, and most particularly also feedback-resistant aspartate kinases resulting in L-lysine. The invention further relates to enzymes having reduced or deactivated feedback inhibition and genes coding therefor, which result in an increased concentration of intermediates of the amino acid or nucleotide synthesis, such as O-acetylhomoserine, cystathionine, orotidine-5'-phosphate, 5-phosphoribosyl diphosphate or inosine-5'-phosphate.

In this way, by way of example, it is possible to obtain mutations in the aspartate kinase gene lysC at nucleotide positions 60, 61, 233, 556 and 982 as indicated in SEQ. ID. NO. 9, with the amino acid exchanges 20, 21, 78, 186, 328 as indicated in SEQ. ID. NO. 10, or at nucleotide positions 60, 61, 932, 1196 as indicated in SEQ. ID. NO. 11, with the amino acid exchanges at positions 20, 21, 311, 399 as indicated in SEQ. ID. NO. 12, or at nucleotide 61 as indicated SEQ. ID. NO. 13, with the amino acid exchanges at positions 21 as indicated in SEQ. ID. NO. 14, or at nucleotide positions 61, 833, 839 as indicated in SEQ. ID. NO. 15, with the amino acid exchanges at positions 21, 278, 280 as indicated in SEQ. ID. NO. 16, or at nucleotide positions 61, 833, 839, 1172 as indicated in SEQ. ID. NO. 33, with the amino acid exchanges at positions 21, 278, 280, 391 as indicated in SEQ. ID. NO. 34, or at nucleotide positions 61 and 932 as indicated in SEQ. ID. NO. 17, with the amino acid exchanges at positions 21 and 311 as indicated in SEQ. ID. NO. 18, or at nucleotide positions 61, 932, 1196 as indicated in SEQ. ID. NO. 19, with the amino acid exchanges at positions 21, 311, 399 as indicated in SEQ. ID. NO. 20, or at nucleotide positions 61 and 1094 as indicated in SEQ. ID. NO. 21, with the amino acid exchanges at positions 21 and 365 as indicated in SEQ. ID. NO. 22, or at nucleotide positions 61, 908 as indicated in SEQ. ID. NO. 29, with the amino acid exchanges at positions 21, 303 as indicated in SEQ. ID. NO. 30, or at nucleotide positions 715 as indicated in SEQ. ID. NO. 31, with the amino acid exchanges at positions 239 as indicated in SEQ. ID. NO. 32, or at nucleotide positions 71, 932, as indicated in SEQ. ID. NO. 23, with the amino acid exchanges at positions 24, 311 as indicated in SEQ. ID. NO. 24, or at nucleotide positions 205, 370, 631, 680, 703, 1049, 1120, as indicated in SEQ. ID. NO. 25, with the amino acid exchanges at positions 69, 124, 211, 227, 235, 350, 374 as indicated in SEQ. ID. NO. 26, as nucleotide positions 476, 1010, 1021 as indicated in SEQ. ID. NO. 27, and with the amino acid exchanges at positions 159, 337, 341 as indicated in SEQ. ID. NO. 28.

It is also possible in each case for only one of the nucleotide and amino acid exchanges per allele and enzyme to be present, or for a plurality to be present, which is to say up to seven, as indicated in SEQ. ID. NO. 25 and SEQ. ID. NO. 26.

Disclaimer:

The invention does not relate to mutations that are known from the prior art listed below, such as mutation lysC A279T described in the application JP 1994062866-A (sequence 1), or lysC A279V from JP 1994261766-A (sequence 3), lysC S301 F from JP 1994261766-A (sequence 4), lysC T3081 from JP 1994261766-A (sequence 5), lysC G345D (Follettie and Sinskey, database entry L16848), lysC R320G, lysC G345D (Jetten et al., database entry L27125), lysC S301 F (U.S. Pat. No. 3,732,144), lysC S381F (EP0435132), lysC S317A (U.S. Pat. No. 5,688,671 (sequence 1)) and also lysC T3801 (WO 01/49854).

The invention also relates to other amino acid exchanges at the positions identified by metabolite sensors and at comparable positions of the enzymes. In the aspartate kinase enzyme of SEQ. ID. NO. 28, for example, where Val can be exchanged with Gly at position 159, preferably any other proteinogenic amino acid is also present, such as Lys, Asn, Arg, Ser, Thr, Ile, Met, Glu, Ala, Val, Gln, His, Pro, Leu, Tyr. Trp, Cys or Phe. In the same enzyme, Asn is exchanged with Ser at position 337, and any other proteinogenic amino acid may also be present at this position, such as Lys, Asn, Arg, Thr, Ile, Met, Glu, Asp, Ala, Val, Gin, His, Pro, Leu, Tyr, Trp, Cys or Phe, or any other proteinogenic amino acid such as Lys, Arg, Ser, Thr, Ile, Met, Glu, Asp, Ala, Val, Gln, His, Pro, Leu, Tyr, Trp, Cys or Phe may be present at position 341 instead of the exchange of Asp with Asn.

According to the invention, the expression "comparable position" shall be understood to mean a position that, by way of comparison of the starting sequence with the comparison sequence using a sequence comparison program (BLAST, Altschul et al. J. Mol. Biol. 1990, 215, 403-410) at the considered position of the starting sequence, supplies an amino acid position in the comparison sequence that differs from the position to be compared by more than ±5, preferably ±4, further preferably ±3, still further preferably ±2, extremely preferably ±1, and most extremely preferably by no position.

The invention will be described in greater detail hereafter based on non-limiting examples.

Example 1

Production of a cell according to the invention based on the first embodiment using the example of a cell in which a gene sequence coding for an enzyme is mutated and selected, so that feedback-resistant enzymes and cells according to the invention containing feedback-resistant enzymes having enhanced performance characteristics are obtained, the enzyme being aspartate kinase.

a) Construction of the Vector pUC18-lysC and Error-Prone PCR of the Aspartate Kinase Gene lysC Using the primer pairs rspl (SEQ. ID. NO. 1) and univ (SEQ. ID. NO. 2) as well as chromosomal DNA of the wild type of *C. glutamicum* ATCC 13032 as templates, the lysC gene coding for the enzyme aspartate kinase was amplified.

```
(SEQ. ID. NO. 1):
GATGGATCCGTGGCCCTGGTCGTACAGAAATATGG (SEQ. ID. NO. 2):
GATGTCGACTTAGCGTCCGGTGCCTGCATAAACG
```

The chromosomal DNA of *C. glutamicum* was isolated as described in Tauch et al. (Tauch et al., 1995, Plasmid 33:168-179). The amplificate was treated with BamHI and SalI and ligated with likewise treated pUC18, and pUC18-lysC was obtained. 10 ng pUC18-lysC was used as the template in each reaction of the error-prone PCR for inserting the mutations, as was 0.1 to 0.8 mM Mn2+, wherein at the lower concentration of below <0.2 mM Mn2+ with Mg2+ an overall concentration of at least 0.2 mM was adjusted. In each reaction, x µl Taq polymerase from Fermentas (Catalog No.: EP0401) was added. The polynucleotides

```
(SEQ. ID. NO. 3): CACAGGAAACAGCTATGACCATG (SEQ. ID. NO. 4): CGCCAGGGTTTTCCCAGTCACGAC
``` were used as primers. The reactions were incubated for 30 minutes. Thereafter, the reaction products were treated with BamHI and SalI and ligated to the likewise treated vector pSen-LysTK(b)-lysC. The ligation products were used to transform *E. coli* DH5amcr (Grant, 1990, Proceedings of the National Academy of Sciences U.S.A., 87:4645-4649). So as to construct the vector pSenLysTK(b)-lysC, the gene lysC was amplified with the preceding 520 bp using the primer pairs LysC-PSLTKC-fw (SEQ. ID. NO. 5) and LysC-PSLTKC-rv (SEQ. ID. NO.6) as well as chromosomal DNA of the wild type of *C. glutamicum* ATCC 13032 as templates. The amplificate was cleaved with XhoI and SalI and ligated to pSenLysTK (WO2011138006) cleaved in SalI.

```
(SEQ. ID. NO. 5):
GCCCTCGAGAAAACAAAAGGCTCAGTCGGAAGACTGGGCCTTTTGTTTTG

GTACCAGCGGCAGCGTGAACATC (SEQ. ID. NO. 6):
GCCGTCGACACGGAATTCAATCTTACGGCCTGCGGAACG
```

The *E. coli* DH5amcr cells transformed with the ligation products were plated out on LB agar plates (Lennox, 1955, Virology, 1:190) containing 40 mg per liter kanamycin.

b) Preparation of the lysC Gene Bank and Transformation of *Corynebacterium glutamicum*

Following overnight incubation of the *E. coli* DH5amcr cells transformed with the ligation products, LB agar plates were washed with 1 ml 0.9% NaCl and the plasmid DNA was prepared using ordinary methods (Sambrook et al., Molecular Cloning. A Laboratory Manual (1989) Cold Spring Harbor Laboratory Press, Cold Spring Harbor, N.Y., USA). This plasmid DNA preparation was used to transform electrocompetent cells of *C. glutamicum* ATCC 13032, as is described in Kirchner, O. and Tauch, A. (J Biotechnol. 2003 Sep. 4; 104(1-3):287-99). The transformed cells were regenerated for 2 hours, then 25 mg per liter kanamycin was added, and 1:10 dilutions of this suspension were incubated for 15 hours in CGXII medium. The CGXII medium is described in Keilhauer et al. in J Bacteriol. 1993 September; 175(17):5595-603.

c) Selection of lysC Muteins

So as to identify and separate the cells with mutated aspartate kinases, the cell suspension was adjusted in CGXII medium to an optical density value of less than 0.1 and directly supplied to the FACS ARIA II high-speed cell sorter (Becton Dickinson GmbH, Tullastr. 8-12, 69126 Heidelberg). The analysis was carried out using excitation wavelengths of 488 and 633 nm, and the detection was carried out at emission wavelengths of 530±15 nm and 660±10 nm at a test pressure of 70 psi. The data was analyzed by way of the software Version BD DIVA 6.1.3 associated with the device. The sheath fluid used was BD FACSflow. Electronic gating was adjusted based on the forward and backward scatter so as to exclude non-bacterial particles. So as to sort EYFP-positive cells, the next stage of electronic gating was selected so as to exclude non-fluorescent cells. Fluorescent cells were sorted on Petri dishes containing Brain Heart Infusion Agar (Difco).

Example 2

Production of a cell according to the invention with feedback-resistant enzymes having enhanced performance characteristics, the enzyme being aspartate kinase and new aspartate kinase sequences.

a) Lysine Formation from Isolated Cells Using Mutated Aspartate Kinase as the Enzyme.

EYFP-positive individual cells sorted on Petri dishes were inoculated in 0.75 ml CGXII medium in microtiter plates of the Flowerplate type. The Flowerplates were procured from m2p-labs GmbH (Aachen) and incubated in a Microtron high-capacity microplate incubator (Infors AG) overnight using a shaking speed of 990 rpm and a shaking radius of 3 mm. Thereafter, a new CGXII medium was inoculated in microtiter plates of the Flowerplate type, and samples were removed after 48 for lysine determination.

The lysine determination was carried out as o-phthaldialdehyde derivative by way of high-pressure liquid chromatography using an UHPLC 1290 Infinity system (Agilent) on a Zorbax Eclipse AAA C18 3.5 micron 4.6×75 mm reversed-phase column and a fluorescence detector. The eluent used was a gradient of 0.01 M Na borate pH 8.2 with increasing methanol concentration, and the detection of the fluorescent isoindole derivatives was carried out at an excitation wavelength of 230 nm and an emission wavelength of 450 nm. The L-lysine values shown in Table 2 were determined, which show an improvement in the L-lysine production compared to the starting strain.

TABLE 2

Strains in which the gene sequence coding for aspartate kinase were mutated with a plasmid, and which were selected for enhanced performance characteristics by way of the metabolite sensor, and excrete L-lysine at an increased rate.

| Strain | L-Lysine (mM) |
|---|---|
| Starting strain ATCC13032 | 0.2 |
| Strain lysC-ls42 | 21.1 |
| Strain lysC-ss77 | 44.9 |
| Strain lysC-ss12 | 20.0 |

TABLE 2-continued

Strains in which the gene sequence coding for aspartate kinase were mutated with a plasmid, and which were selected for enhanced performance characteristics by way of the metabolite sensor, and excrete L-lysine at an increased rate.

| Strain | L-Lysine (mM) |
|---|---|
| Strain lysC-is90 | 39.0 |
| Strain lysC-ls2 | 24.9 |
| Strain lysC-ss92 | 44.3 |
| Strain lysC-ls15 | 27.1 |
| Strain lysC-ls57 | 29.5 |
| Strain lysC-ss91 | 14.0 |
| Strain lysC-ls1 | 19.7 |
| Strain lysC-ls8 | 23.0 |
| Strain lysC-ss63 | 32.5 |
| Strain lysC-ls56 | 30.9 | b) Determination of the Sequences of the Aspartate Kinases

A colony PCR was carried out on the strains shown in Table 2, as described in Lee and Cooper (Improved screen for bacterial colonies, Biotechniques 18(2):225-226). For this purpose, the following two primers were used:

(SEQ. ID. NO. 7): TGAGACGCATCCGCTAAAGCC (SEQ. ID. NO. 8): ATCTTACGGCCTGCGGAACGTG

The amplificates were purified with the QIAquick PCR Purification Kit from Qiagen (Catalog No. 28104) and sequenced by the company GATC. The resulting DNA sequences were then analyzed using known algorithms or the GCG sequence analysis program from Butler (Methods of Biochemical Analysis 39, 74-97 (1998)), the FASTA algorithm from Pearson and Lipman (Proceedings of the National Academy of Sciences USA 85, 2444-2448 (1988)) or the BLAST algorithm from Altschul et al. (Nature Genetics 6, 119-129 (1994)) and compared to the sequence entries present in publicly accessible databases (EMBL, Heidelberg, Germany; NCBI, Bethesda, Md., USA).

The sequence identification numbers (SEQ. ID. NO.) of lysC alleles from the respective strains mentioned in Table 2 which contain the plasmids with the lysC alleles in pSenLysTK(b) are indicated in Table 3. In addition, the sequence identification numbers (SEQ. ID. NO.) of the aspartate kinase polypeptide sequences are also listed there. Furthermore the nucleotide exchanges of the lysC alleles with information as to the position in the polynucleotide sequence are listed, as are the amino acid exchanges of the lysC polypeptides with information as to the position in the polypeptide sequence.

TABLE 3

Nucleotide sequences and polypeptide sequences of the enzyme aspartate kinase, which result in enhanced performance characteristics.

| | Allele | Nucleotide exchange(s) | | Polypeptide | Amino acid exchange(s) |
|---|---|---|---|---|---|
| SEQ. ID. NO. 9 | lysC-ls42 | a60c, a61g, a233g, a556g, a982g | SEQ. ID. NO. 10 | LysC-ls42 | R20S, N21D, N78S, I186V, K328E |
| SEQ. ID. NO. 11 | lysC-ss77 | a60c, a61g, c932t, g1196t | SEQ. ID. NO. 12 | LysC-ss77 | R20S, N21D, T311I, R399L |
| SEQ. ID. NO. 13 | lysC-ss12 | a61g | SEQ. ID. NO. 14 | LysC-ss12 | N21D |
| SEQ. ID. NO. 15 | lysC-ls90 | a61g, a833g, c839t | SEQ. ID. NO. 16 | LysC-ls90 | N21D, E278G, A280V |
| SEQ. ID. NO. 17 | lysC-ss92 | a61g, c932t | SEQ. ID. NO. 18 | LysC-ss92 | N21D, T311I |
| SEQ. ID. NO. 19 | lysC-ls15 | a61g, c932t, g1196t | SEQ. ID. NO. 20 | LysC-ls15 | N21D, T311I, R399L |
| SEQ. ID. NO. 21 | lysC-ls57 | a61g, t1094a | SEQ. ID. NO. 22 | LysC-ls57 | N21D, M365K |
| SEQ. ID. NO. 23 | lysC-ls8 | a71g, c932t | SEQ. ID. NO. 24 | LysC-ls8 | E24G, T311I |
| SEQ. ID. NO. 25 | lysC-ss63 | c205t, g370c, a631g, t680c, a703g, t1049c, a1120g | SEQ. ID. NO. 26 | LysC-ss63 | L69F, I24P, 211V, L227P, 235D, 350A, 374D |
| SEQ. ID. NO. 27 | lysC-ls56 | t476g, a1010g, g1021a | SEQ. ID. NO. 28 | LysC-ls56 | V159E, N337S, D341N |
| SEQ. ID. NO. 29 | lysC-ss91 | a61g, t908c | SEQ ID NO. 30 | LysC-ss91 | N21D, V303A |
| SEQ. ID. NO. 31 | lysC-ls1 | a715g | SEQ. ID. NO. 32 | LysC-ls1 | T239A |
| SEQ. ID. NO. 33 | lysC-ls2 | a61g, a833g, c839t, a1172g | SEQ. ID. NO. 34 | LysC-ls2 | N21D, E278G, A280V, E391G |

---

The invention claimed is:

1. A method for producing vectors encoding a feedback inhibited enzyme, the enzyme comprising a mutation resulting in the enzyme having reduced or deactivated feedback inhibition by a metabolite, wherein the method comprises
mutating genes encoding the feedback-inhibited enzyme in vitro,
ligating the mutated genes into vectors wherein the ligated mutated genes are each operably linking to an expression control sequence,
transforming the ligated vectors into a population of microorganisms that each contain a fluorescent metabolite sensor which synthesizes a fluorescent protein in the presence of the metabolite wherein microorganisms comprising the ligated vectors with the mutations resulting in the enzyme having reduced or deactivated feedback inhibition synthesize the fluorescent protein at increased concentration compared to the concentration of fluorescent protein in a non-transformed cell presence of the vector comprising and isolating said plurality of microorganisms exhibiting the increased fluorescent protein concentration, and
wherein the vectors encoding the enzyme having reduced or deactivated feedback inhibition are isolated from the plurality of microorganisms having the increased fluorescence, and wherein the metabolite sensor comprises at least one metabolite sensor selected from the group of pSenLys, pSenArg, pSenSer, pSenOAS and pJC1-lrp-brnF-eyfp.

2. The method according to claim 1, wherein said mutating comprises random mutagenesis.

3. The method according to claim 1 wherein the vectors comprise at least one of a plasmid, an insertion element, a transposon and a phage.

4. The method according to claim 1, wherein the gene encoding the feedback-inhibited enzyme is from a yeast or a bacterium.

5. The method according to claim 1, wherein the feedback inhibited enzyme is 2-isopropylmalate synthase, acetohydroxy acid synthase, acetylglutamate synthase, anthranilate synthase, asparagine synthetase, aspartate transcarbamylase, aspartate kinase, ATP-phosphoribosyl transferase, carbamoyl phosphate synthetase, chorismatemutase I, chorismatemutase II, cysteine synthase, D-3-phosphoglycerate dehydrogenase, 3-deoxy-D-arabino-heptulosonate-7-phosphate synthase, dihydrodipicolinate synthase, glutamate dehydrogenase, glutamate synthase, glutamine synthetase, glutamyl kinase, homocysteinetransmethylase, homoserine O-acetyltransferase, homoserine O-succinyltransferase, homoserine dehydrogenase, methionine synthase, phosphoribosylphrophosphate synthase, prephenate dehydrogenase I, prephenate dehydrogenase II, pyrroline-5-carboxylate reductase, ribose 1,5-bisphosphokinase, serinace-tyl(succinyl) transferase, threonine ammoniumlyase or tyrosine aminotransferase.

6. The method according to claim 1, wherein isolating said plurality of microorganisms exhibiting the increase fluorescent protein concentration comprises selecting for isolation microorganisms from among said plurality of microorganisms that have relatively highest fluorescence.

7. The method according to claim 1, wherein production of the isolated vectors is achieved by transforming the isolated vectors into a population of second microorganisms.

8. The method according to claim 1, wherein the genes encoding the enzyme with reduced or deactivated feedback inhibition are isolated from the vectors and sub-cloned into a second set of vectors for improved expression of the enzymes wherein the second set of ligated vectors are transformed into a production strain.

9. The method according to claim 1, wherein the genes encoding the enzyme having reduced or deactivated feedback inhibition are introduced into the chromosome of a production strain.

10. The method according to claim 1, wherein the population of microorganism containing the gene encoding the enzyme having reduced or deactivated feedback inhibition is a bacterium or a yeast.

11. The method for producing vectors according to claim 1, wherein the isolated plurality of microorganisms further comprises a biosynthesis pathway for an amino acid or a nucleotide wherein the mutation results in enhanced production of the amino acid or the nucleotide.

12. The method according to claim 11, wherein the produced amino acid comprises at least one component from the group comprising L-valine, L-leucine, L-asparagine, L-lysine, L-methionine, L-threonine, L-isoleucine, L-histidine, L-glutamate, L-glutamine, proline, L-arginine, L-tryptophan, L-tyrosine, L-phenylalanine, L-serine and L-cysteine.

13. The method according to claim 11, wherein the produced nucleotide comprises at least one component from the group comprising orotidine-5'-phosphate, 5-phosphoribosyl diphosphate or inosine-5'-phosphate.

* * * * *